US012329925B2

(12) United States Patent
Jiang et al.

(10) Patent No.: US 12,329,925 B2
(45) Date of Patent: Jun. 17, 2025

(54) UNIVERSAL CAP WITH PRESSURE SEAL

(71) Applicant: Becton, Dickinson and Company, Franklin Lakes, NJ (US)

(72) Inventors: Chang Jiang, Butler, NJ (US); Saravanababu Murugesan, East Windsor, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 723 days.

(21) Appl. No.: 17/631,662

(22) PCT Filed: Aug. 5, 2020

(86) PCT No.: PCT/US2020/044951
§ 371 (c)(1),
(2) Date: Jan. 31, 2022

(87) PCT Pub. No.: WO2021/026199
PCT Pub. Date: Feb. 11, 2021

(65) Prior Publication Data
US 2022/0273931 A1 Sep. 1, 2022

Related U.S. Application Data

(60) Provisional application No. 62/884,285, filed on Aug. 8, 2019.

(51) Int. Cl.
*A61M 39/16* (2006.01)
*A61M 39/20* (2006.01)

(52) U.S. Cl.
CPC .......... *A61M 39/162* (2013.01); *A61M 39/20* (2013.01)

(58) Field of Classification Search
CPC .... A61M 39/16; A61M 39/20; A61M 39/162; A61M 39/165
See application file for complete search history.

(56) References Cited

U.S. PATENT DOCUMENTS

| 4,597,758 A | 7/1986 | Aalto et al. |
| 4,711,363 A | 12/1987 | Marino |

(Continued)

FOREIGN PATENT DOCUMENTS

| CA | 2523133 C | 2/2013 |
| CN | 1322119 A | 11/2001 |

(Continued)

OTHER PUBLICATIONS

"Ruhof Dry Sponges", Ruhof, Sep. 30, 2016, https://www.ruhof.com/products/ruhof-dry-sponges (Year: 2016).

(Continued)

*Primary Examiner* — Laura A Bouchelle
(74) *Attorney, Agent, or Firm* — Servilla Whitney LLC

(57) ABSTRACT

A cap for connection to a medical connector comprises: a housing, a protrusion, a disinfection sponge, and a pressure seal. The protrusion includes an inner thread on an inner surface, the inner thread being sufficient to interlock with a mating feature of a female medical connector. The inner surface of the protrusion defines a second cavity. The protrusion includes an outer thread on an outer surface, the outer thread being sufficient to interlock with a mating feature of a male medical connector. The disinfection sponge is disposed on the second cavity. The pressure seal is attached to the housing and disposed adjacent to a surface of the disinfection sponge. The pressure seal can comprise a flexible insert attached to an interior surface of the top wall of the housing. The pressure seal can comprise a combination of: an elongate member and an insert that is slidably engaged with the elongate member.

29 Claims, 16 Drawing Sheets

(56) References Cited

U.S. PATENT DOCUMENTS

| | | | |
|---|---|---|---|
| 4,738,376 A | 4/1988 | Markus | |
| 5,496,288 A | 3/1996 | Sweeney | |
| 5,676,406 A | 10/1997 | Simmons et al. | |
| 6,632,199 B1 | 10/2003 | Tucker et al. | |
| 7,316,669 B2* | 1/2008 | Ranalletta | A61M 5/3134 604/199 |
| 8,388,894 B2 | 3/2013 | Colantonio | |
| 8,715,231 B2 | 5/2014 | Woehr | |
| 8,721,627 B2 | 5/2014 | Alpert et al. | |
| 9,039,989 B2* | 5/2015 | Liu | A61M 39/162 422/300 |
| 9,132,223 B1 | 9/2015 | Wakeel | |
| 9,192,449 B2 | 11/2015 | Kerr et al. | |
| 9,283,369 B2* | 3/2016 | Ma | A61M 39/20 |
| 9,867,975 B2* | 1/2018 | Gardner | A61M 39/20 |
| 10,166,381 B2* | 1/2019 | Gardner | A61M 39/162 |
| 10,376,686 B2 | 8/2019 | Burkholz et al. | |
| 10,871,246 B2 | 12/2020 | Marici et al. | |
| 11,353,147 B2 | 6/2022 | Marici | |
| 11,511,100 B2 | 11/2022 | Ryan | |
| 11,628,288 B1 | 4/2023 | Solomon et al. | |
| 2004/0039341 A1 | 2/2004 | Ranalletta | |
| 2004/0044318 A1 | 3/2004 | Fiser et al. | |
| 2005/0197646 A1 | 9/2005 | Connell et al. | |
| 2007/0060904 A1 | 3/2007 | Vedrine et al. | |
| 2008/0010766 A1 | 1/2008 | Kaufman et al. | |
| 2008/0177250 A1 | 7/2008 | Howlett et al. | |
| 2010/0003067 A1 | 1/2010 | Shaw et al. | |
| 2010/0049170 A1 | 2/2010 | Solomon et al. | |
| 2010/0050351 A1 | 3/2010 | Colantonio et al. | |
| 2010/0100056 A1 | 4/2010 | Cawthon et al. | |
| 2011/0046603 A1 | 2/2011 | Felsovalyi et al. | |
| 2011/0054440 A1 | 3/2011 | Lewis | |
| 2011/0213341 A1 | 9/2011 | Solomon et al. | |
| 2011/0264037 A1 | 10/2011 | Foshee et al. | |
| 2012/0039764 A1 | 2/2012 | Solomon et al. | |
| 2012/0111368 A1 | 5/2012 | Rahimy et al. | |
| 2012/0123386 A1 | 5/2012 | Tsals | |
| 2012/0302997 A1 | 11/2012 | Gardner et al. | |
| 2013/0085474 A1 | 4/2013 | Charles et al. | |
| 2013/0171030 A1 | 7/2013 | Ferlic et al. | |
| 2013/0197485 A1 | 8/2013 | Gardner et al. | |
| 2013/0338644 A1 | 12/2013 | Solomon et al. | |
| 2014/0052074 A1 | 2/2014 | Tekeste | |
| 2014/0150832 A1 | 6/2014 | Rogers et al. | |
| 2014/0366914 A1 | 12/2014 | Kerr et al. | |
| 2015/0011936 A1 | 1/2015 | Okihara et al. | |
| 2015/0094666 A1 | 4/2015 | Bates et al. | |
| 2016/0045629 A1 | 2/2016 | Gardner et al. | |
| 2016/0067422 A1 | 3/2016 | Davis et al. | |
| 2016/0158520 A1 | 6/2016 | Ma et al. | |
| 2017/0203087 A1 | 7/2017 | Ryan et al. | |
| 2018/0085568 A1 | 3/2018 | Drmanovic | |
| 2018/0200145 A1 | 7/2018 | Sanders et al. | |
| 2018/0214684 A1 | 8/2018 | Avula et al. | |
| 2018/0237190 A1 | 8/2018 | Iwasaki | |
| 2018/0243547 A1 | 8/2018 | Fox et al. | |
| 2018/0256879 A1 | 9/2018 | Chiu et al. | |
| 2018/0256883 A1 | 9/2018 | Follman et al. | |
| 2019/0000115 A1 | 1/2019 | Ma et al. | |
| 2019/0001115 A1 | 1/2019 | Ma et al. | |
| 2019/0151643 A1 | 5/2019 | Alpert | |
| 2019/0234540 A1 | 8/2019 | Marici et al. | |
| 2019/0351212 A1 | 11/2019 | Dudar et al. | |
| 2020/0147360 A1 | 5/2020 | Arnett et al. | |
| 2021/0100996 A1 | 4/2021 | Wijesuriya et al. | |
| 2021/0187267 A1 | 6/2021 | Jiang | |
| 2022/0273931 A1 | 9/2022 | Jiang et al. | |
| 2023/0080687 A1 | 3/2023 | Ryan | |

FOREIGN PATENT DOCUMENTS

| | | |
|---|---|---|
| CN | 101980746 A | 2/2011 |
| CN | 201807018 U | 4/2011 |
| CN | 102188766 A | 9/2011 |
| CN | 102448502 A | 5/2012 |
| CN | 103083767 A | 5/2013 |
| CN | 204161736 U | 2/2015 |
| CN | 206198472 U | 5/2017 |
| CN | 216022674 U | 3/2022 |
| CN | 110090354 B | 1/2023 |
| DE | 20017013 U1 | 12/2000 |
| DE | 10247963 A1 | 5/2004 |
| EP | 0589379 A1 | 3/1994 |
| EP | 2606930 A1 | 6/2013 |
| EP | 2832391 A1 | 2/2015 |
| EP | 3275490 A1 | 1/2018 |
| GB | 2408259 A | 5/2005 |
| GB | 2518646 A | 4/2015 |
| JP | 103139363 A | 6/1991 |
| JP | H04501672 A | 3/1992 |
| JP | 2001502191 A | 2/2001 |
| JP | 2001521792 A | 11/2001 |
| JP | 2004208740 A | 7/2004 |
| JP | 2008239164 A | 10/2008 |
| JP | 2008253775 A | 10/2008 |
| JP | 2009526241 A | 7/2009 |
| JP | 2010527276 A | 8/2010 |
| JP | 2012522593 A | 9/2012 |
| JP | 2013509274 A | 3/2013 |
| JP | 2014528288 A | 10/2014 |
| JP | 2014532517 A | 12/2014 |
| JP | 2015517377 A | 6/2015 |
| JP | 2016511111 A | 4/2016 |
| JP | 2016511119 A | 4/2016 |
| JP | 2016104214 A | 6/2016 |
| JP | 7419237 B2 | 1/2024 |
| WO | 200024442 A1 | 5/2000 |
| WO | 200224551 A1 | 3/2002 |
| WO | 2011066586 A1 | 6/2011 |
| WO | 2012144026 A1 | 10/2012 |
| WO | 2013046857 A1 | 4/2013 |
| WO | 2014159346 A1 | 10/2014 |
| WO | 2015174953 A1 | 11/2015 |
| WO | 2016158144 A1 | 10/2016 |
| WO | 2017087400 A1 | 5/2017 |
| WO | 2018106508 A1 | 6/2018 |
| WO | 2018237090 A1 | 12/2018 |
| WO | 2019147906 A1 | 8/2019 |
| WO | 2019152482 A1 | 8/2019 |
| WO | 2020056120 A1 | 3/2020 |
| WO | 2020112767 A1 | 6/2020 |

OTHER PUBLICATIONS

Final Office Action in U.S. Appl. No. 17/229,173 dated May 22, 2024, 28 pages.

Non-Final Office Action in U.S. Appl. No. 16/923,238 dated Feb. 28, 2024, 18 pages.

PCT International Search Report and Written Opinion in PCT/US2020/044951 dated Oct. 14, 2020, 14 pages.

* cited by examiner

UNIVERSAL CAP WITH PRESSURE SEAL

CROSS-REFERENCE TO RELATED APPLICATIONS

This application is the National Stage entry of PCT/US2020/044951, filed on Aug. 5, 2020, which claims priority to U.S. Provisional Application Ser. No. 62/884,285, filed Aug. 8, 2019, the entire disclosures of which are hereby incorporated by reference herein.

TECHNICAL FIELD

The present disclosure generally relates to a device for disinfecting and sterilizing access ports with, e.g., male and female Luer fitting, and, in particular, to disinfecting and sterilizing devices capable of accommodating multiple types of connectors. Generally, embodiments herein relate to the fields of threaded fitting, including medical caps and medical disinfection caps, and in particular caps and/or disinfection caps for uses with fluid Luer connectors.

BACKGROUND

Vascular access devices (VAD's) are commonly used therapeutic devices and include intravenous (IV) catheters. There are two general classifications of VAD's: peripheral catheters and central venous catheters. Bacteria and other microorganisms may gain entry into a patient's vascular system from access hubs and ports/valves upon connection to the VAD to deliver the fluid or pharmaceutical. Each access hub (or port/valve or connection) is associated with some risk of transmitting a catheter related bloodstream infection (CRBSI), which can be costly and potentially lethal.

In order to decrease CRBSI cases and to ensure VAD's are used and maintained correctly, standards of practice have been developed, which include disinfecting and cleaning procedures.

Disinfection caps have been added to the Society for Healthcare Epidemiology of America (SHEA) guidelines and early indications are that caps will also be incorporated into the 2016 Infusion Nurses Standards (INS) guidelines.

In developed markets, when utilizing an IV catheter, a needleless connector will typically be used to close off the system and then subsequently accessed to administer medication or other necessary fluids via the catheter to the patient. INS Standards of Practice recommend the use of a needleless connector and state that it should be "consistently and thoroughly disinfected using alcohol, tincture of iodine or chlorhexidine gluconate/alcohol combination prior to each access." The disinfection of the needleless connector is ultimately intended to aid in the reduction of bacteria that could be living on the surface and possibly lead to a variety of catheter related complications including CRBSI. Nurses will typically utilize a 70% isopropyl alcohol (IPA) pad to complete this disinfection task by doing what is known as "scrubbing the hub." However, compliance to this practice is typically very low. In addition to a lack of compliance to "scrubbing the hub", it has also been noted through clinician interviews that there is often a variation in scrub time, dry time and the number of times the needleless connector is scrubbed.

Throughout the sequence of procedures associated with the transmission of a microorganism that can cause a CRBSI, there are many risks of contact or contamination. Contamination can occur during drug mixing, attachment of a cannula, and insertion into the access hub. Because the procedure to connect to a VAD is so common and simple, the risk associated with entry into a patient's vascular system has often been overlooked. Presently, the risk to hospitals and patients is a substantial function of the diligence of the clinician performing the connection, and this diligence is largely uncontrollable.

Currently, caps for male needleless connectors, female needleless connectors, intravenous (IV), and hemodialysis lines use different designs and are, therefore, limited to the types of connectors to which the cap can be attached. Currently, there are male disinfecting cap devices for disinfecting ISO594-2 type of female threaded fluid Luer connectors and there are female disinfecting cap devices for disinfecting ISO594-2 type of male threaded fluid Luer connectors. However there is not a singular universal disinfecting cap device with features allowing it to interface with either a male or female type of threaded connectors. Thus, prior disinfecting caps were designed to fit one type of connector only, and were specific to one particular size and/or shape of connector. Thus, there is a need for a disinfecting device capable of accommodating multiple types of connectors, including both male and female connectors, to streamline the disinfecting process.

Further to providing disinfecting devices, disinfectant ingress is a consideration because ingress of disinfectant can compromise safety to patients. Disinfectant ingress is to be mitigated to non-toxic levels according to toxicology standards. While needleless connectors have septa in them to form a closed system by themselves, there is a need for disinfecting caps used with medical connectors such as male connectors on IV tubing end and open female Luer ports on catheters and stopcocks, to minimize ingress of disinfectant, such as isopropyl alcohol or chlorhexidine, into the central lumen of the connectors.

SUMMARY

Aspects of the disclosure pertain to caps for use with medical connectors.

In an aspect, a cap comprises: a housing comprising: a top wall; an essentially cylindrical sidewall forming a first cavity; and an open bottom formed by the cylindrical sidewall with an opening to the first cavity within the housing for receiving a hub of a medical connector; and a protrusion extending from the housing and positioned within the first cavity, the protrusion having an inner surface and an outer surface, the inner surface of the protrusion defining a second cavity, an inner thread on the inner surface of the protrusion, the inner thread being sufficient to interlock with a threaded fitting of a female medical connector, and an outer thread on the outer surface of the protrusion, the outer thread being sufficient to interlock with a threaded fitting of a male medical connector; a disinfection sponge configured within the second cavity; and a pressure seal attached to the housing and disposed adjacent to a surface of the disinfection sponge.

In one or more embodiments, upon engagement of the cap with the medical connector, the disinfection sponge contacts a lumen edge of the medical connector and the pressure seal blocks a lumen of the medical connector thereby inhibiting disinfectant ingress into the lumen.

In one or more embodiments, the lumen of the medical connector is open to the cap, the pressure seal enters the lumen to inhibit disinfectant ingress into the lumen.

In one or more embodiments, when the medical connector comprises a septum in the lumen, the pressure seal is positioned to avoid creating a fluid path through the septum.

In one or more embodiments, the disinfection sponge comprises a slotted end; an essentially cylindrical sponge sidewall defining a hollow and an open end; and a sponge end wall.

In one or more embodiments, the slotted end of the disinfection sponge comprises a slot that extends into opposing portions of the sponge sidewall.

In one or more embodiments, the slot extends along opposing portions of the sponge sidewall to the open end.

In one or more embodiments, the pressure seal is disposed in the hollow of the disinfection sponge.

In one or more embodiments, in an uncompressed state, the pressure seal is disposed entirely in the hollow.

In one or more embodiments, the sponge end wall is in direct contact with an interior surface of the top wall.

In one or more embodiments, the pressure seal comprises an elongate member and an insert, wherein: the elongate member extends from an interior surface of the top wall of the housing; and the insert comprises: a bottom wall, and an essentially cylindrical insert sidewall, the insert sidewall forming a chamber and a top edge of the insert sidewall defining an aperture; the insert slidably engaging with the elongate member.

In one or more embodiments, an inside surface of the top edge slidably engages with the elongate member.

In one or more embodiments, the elongate member comprises a shoulder section, a slanted section, and one or more sliding sections.

In one or more embodiments, the insert comprises a plurality of prongs defined by portions of the insert sidewall and the top edge separated by slits.

In one or more embodiments, faces of the prongs slidably engage with the elongate member.

In one or more embodiments, an outside geometry of the insert sidewall comprises a tapered surface effective to complement an inner surface of a lumen of the medical connector.

In one or more embodiments, the insert comprises a polymeric material selected from the group consisting of polyethylene, polypropylene, thermoplastic elastomer (TPE), or combinations thereof.

In one or more embodiments, the pressure seal comprises a flexible insert attached to an interior surface of the top wall of the housing.

In one or more embodiments, the flexible insert comprises an elastomeric polymeric material.

In one or more embodiments, the flexible insert comprises a top wall, a bottom wall, and an essentially cylindrical and porous insert sidewall extending between the top wall and the bottom wall.

In one or more embodiments, the top wall of the flexible insert further comprises an extension that engages with an upper lip the protrusion.

In one or more embodiments, the flexible insert is breathable.

Another aspect provides: a cap comprising: a housing comprising: a top wall; an essentially cylindrical sidewall forming a first cavity; and an open bottom formed by the cylindrical sidewall with an opening to the first cavity within the housing for receiving a hub of a medical connector; and a protrusion extending from the housing and positioned within the first cavity, the protrusion having an inner surface and an outer surface, the inner surface of the protrusion defining a second cavity, an inner thread on the inner surface of the protrusion, the inner thread being sufficient to interlock with a mating feature of the medical connector comprising a female medical connector, and an outer thread on the outer surface of the protrusion, the outer thread being sufficient to interlock with a mating feature of the medical connector comprising a male medical connector; a disinfection sponge configured within the second cavity, the disinfection sponge comprising a slotted end; an essentially cylindrical sponge sidewall defining a hollow and an open end; and a sponge end wall; and a pressure seal disposed in the hollow of the disinfection sponge, the pressure seal comprising: an elongate member extending from an interior surface of the top wall of the housing; and an insert comprising a bottom wall, and an essentially cylindrical insert sidewall, the insert sidewall forming a chamber and a top edge of the insert sidewall defining an aperture; the insert slidably engaging with the elongate member; wherein upon engagement of the cap with the medical connector, the disinfection sponge contacts a lumen edge of the medical connector and the insert of the pressure seal blocks a lumen of the medical connector thereby inhibiting disinfectant ingress into the lumen.

In one or more embodiments, an inside surface of the top edge slidably engages with the elongate member.

In one or more embodiments, the elongate member comprises a shoulder section, a slanted section, and one or more sliding sections.

In one or more embodiments, the insert sidewall comprises a plurality of prongs defined by portions of the insert sidewall and the top edge separated by slits.

In one or more embodiments, faces of the prongs slidably engage with the elongate member.

In one or more embodiments, an outside geometry of the insert sidewall comprises a tapered surface effective to compliment an inner surface of a lumen of the medical connector.

In one or more embodiments, the insert comprises a polymeric material selected from the group consisting of polyethylene, polypropylene, thermoplastic elastomer (TPE), or combinations thereof.

Another aspect is a cap comprising: a housing comprising: a top wall; an essentially cylindrical sidewall forming a first cavity; and an open bottom formed by the cylindrical sidewall with an opening to the first cavity within the housing for receiving a hub of a medical connector; and a protrusion extending from the housing and positioned within the first cavity, the protrusion having an inner surface and an outer surface, the inner surface of the protrusion defining a second cavity, an inner thread on the inner surface of the protrusion, the inner thread being sufficient to interlock with a mating feature of the medical connector comprising a female medical connector, and an outer thread on the outer surface of the protrusion, the outer thread being sufficient to interlock with a mating feature of the medical connector comprising a male medical connector; a disinfection sponge configured within the second cavity, the disinfection sponge comprising a slotted end; an essentially cylindrical sponge sidewall defining a hollow and an open end; and a sponge end wall; and a pressure seal disposed in the hollow of the disinfection sponge, the pressure seal comprising: a flexible insert attached to an interior surface of the top wall of the housing; wherein upon engagement of the cap with the medical connector, the disinfection sponge contacts a lumen edge of the medical connector and the pressure seal blocks a lumen of the medical connector thereby inhibiting disinfectant ingress into the lumen.

In one or more embodiments, the flexible insert comprises an elastomeric polymeric material.

In one or more embodiments, the flexible insert comprises a top wall, a bottom wall, and an essentially cylindrical and porous insert sidewall extending between the top wall and the bottom wall.

In one or more embodiments, the top wall of the flexible insert further comprises an extension that engages with an upper lip the protrusion.

In one or more embodiments, the flexible insert is breathable.

In one or more embodiments, the medical connector is selected from a male Luer connector, a female Luer connector, and a needleless connector.

In one or more embodiments, the disinfection sponge comprises a disinfectant, an antimicrobial agent, or combinations thereof.

In one or more embodiments, the disinfectant or the antimicrobial agent is selected from the group consisting essentially of: isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

In one or more embodiments, the disinfectant or antimicrobial agent comprises at least one of chlorhexidine gluconate and chlorhexidine diacetate.

In one or more embodiments, the protrusion is integrally-formed with the housing.

In one or more embodiments, the protrusion is attached to an interior surface of the top wall of the housing.

In one or more embodiments, the protrusion is snap-fix or adhered to the interior surface of the top wall of the housing.

In one or more embodiments, the protrusion comprises an upper lip that engages with an elongate ring extending from an inner surface of the top wall of the housing.

A further aspect is: a method of disinfecting a medical connector comprising: connecting the cap of any preceding embodiment to a medical connector by engaging threads of the medical connector onto the inner thread or the outer thread of the protrusion such that an edge of the medical connector contacts the disinfection sponge and the pressure seal inhibits disinfectant ingress into a lumen of the medical connector.

An aspect provides a medical assembly comprising the cap of any of embodiment disclosed herein.

In one or more embodiments, the medical connector is a female medical connector with a male threaded fitting selected from the group consisting of: a needleless connector, a stopcock, a female Luer connector, and a catheter connector.

In one or more embodiments, the medical connector is a male medical connector with a female threaded fitting selected from the group consisting of: an intravenous tubing end and a male Luer connector.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims, or may be learned by the practice of the disclosure as set forth hereinafter.

DETAILED DESCRIPTION

Figure 1:
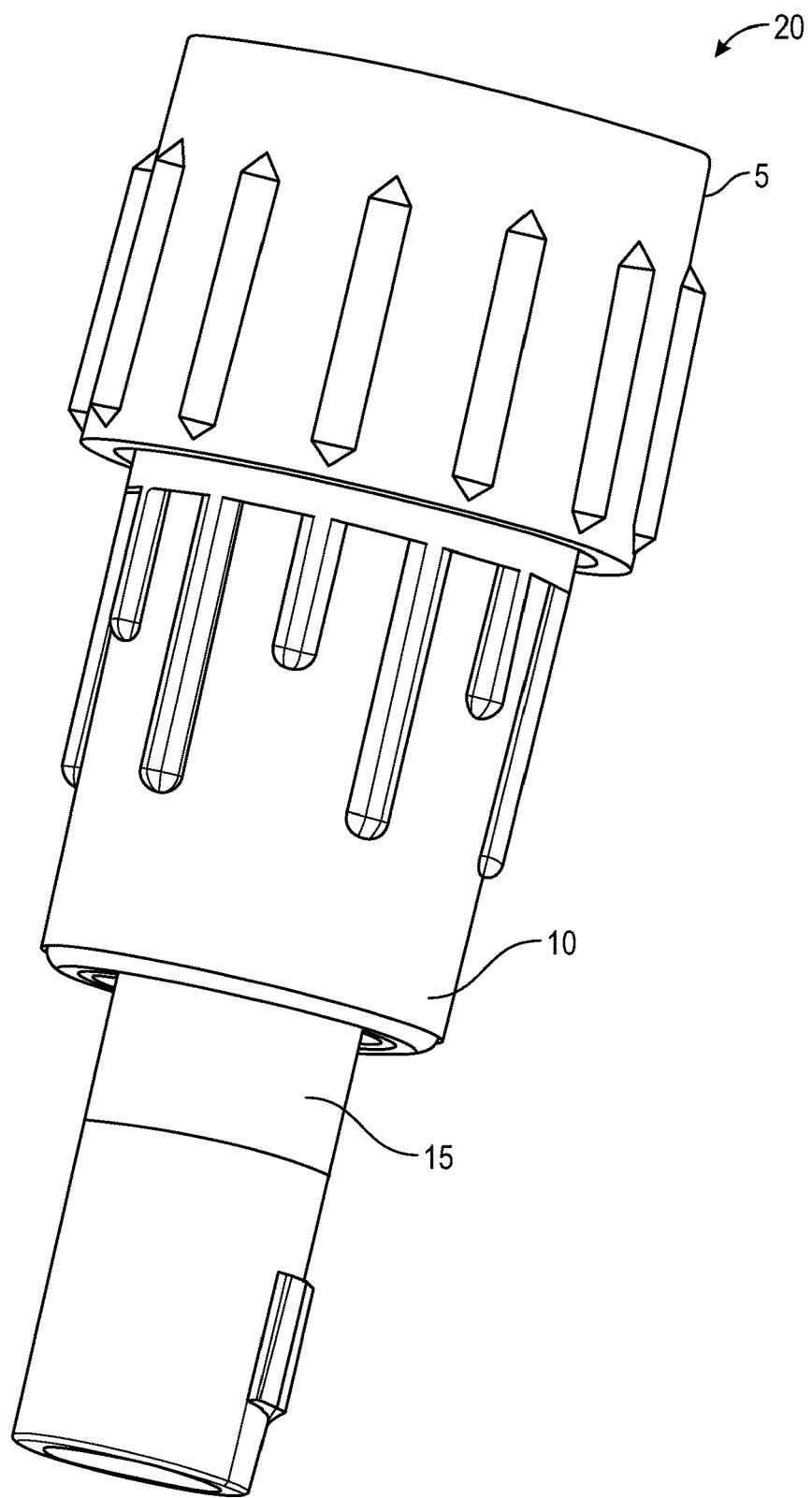
FIG. 1 illustrates a perspective side view of an exemplary medical assembly according to an embodiment.

Embodiments of the disclosure pertain to a sterile, universal cap with pressure seal for connection to and disinfection of a medical connector, including male connectors and female connectors. The male connectors and female connectors can be male Luer connectors and female Luer connectors. Embodiments of the cap comprise a housing, a protrusion, a disinfection sponge, and a pressure seal. The cap comprises housing having a closed end and an open end. The sidewall of the housing has a length extending from the closed end to an open end and defining a chamber. In one or more embodiments, the open end includes a peripheral ledge extending radially outward from the open end defining an end face and an engagement surface. The protrusion has an inner surface having one or more threads to engage male threads of a female medical connector, for example, a female Luer connector. An outer surface of the protrusion has one or more threads to engage female threads of a male medical connector, for example, a male Luer connector. The disinfection sponge is located in a cavity defined by the inner surface of the protrusion. The pressure seal is attached to the housing and disposed adjacent to a surface of the disinfection sponge. In an embodiment, the pressure seal comprises a flexible insert attached to an interior surface of the top wall of the housing. In another embodiment, the pressure seal comprises a combination of: an elongate member and an insert. The elongate member extends from an interior surface of the top wall of the housing; and can be integrally-formed with the housing; and the insert can be a slidable insert that is slidably engaged with the elongate member.

The universal disinfecting caps with pressure seals disclosed herein are advantageous because the inclusion of a pressure seal minimizes ingress of disinfectant, such as isopropyl alcohol or chlorhexidine, into the central lumen of medical connectors. These caps may be used with medical connectors, such as male connectors on IV tubing end and open female Luer ports on catheters and stopcocks.

In addition, the universal disinfecting caps with pressure seals disinfecting caps herein have the benefit of being capable of holding pressure which can mitigate and/or prevent fluid leakage, waste of medication, spill of hazardous drug, or even patients losing blood, which can happen under some circumstances, e.g., by non-compliance or by accident, when clamps and/or rollers on IV tubing or valves on stopcocks are not fully closed.

With respect to terms used in this disclosure, the following definitions are provided.

As used herein, the use of "a," "an," and "the" includes the singular and plural.

As used herein, the term "catheter related bloodstream infection" or "CRBSI" refers to any infection resulting from the presence of a catheter or IV line.

As used herein, the term "Luer connector" refers to a connection collar that is the standard way of attaching syringes, catheters, hubbed needles, IV tubes, etc. to each other. The Luer connector consists of male and female interlocking tubes, slightly tapered to hold together better with even just a simple pressure/twist fit. Luer connectors can optionally include an additional outer rim of threading, allowing them to be more secure. The Luer connector male end is generally associated with a flush syringe and can interlock and connect to the female end located on the vascular access device (VAD). A Luer connector comprises a distal end, a proximal end, an irregularly shaped outer wall, a profiled center passageway for fluid communication from the chamber of the barrel of a syringe to the hub of a VAD. A Luer connector also has a distal end channel that releasably attaches the Luer connector to the hub of a VAD, and a proximal end channel that releasably attaches the Luer connector to the barrel of a syringe.

As would be readily appreciated by skilled artisans in the relevant art, while descriptive terms such as "lock", "hole", "tip", "hub", "thread", "sponge", "prong", "protrusion", "tab", "slope", "wall", "top", "side", "bottom" and others are used throughout this specification to facilitate understanding, it is not intended to limit any components that can be used in combinations or individually to implement various aspects of the embodiments of the present disclosure.

The matters exemplified in this description are provided to assist in a comprehensive understanding of exemplary embodiments of the disclosure. Accordingly, those of ordinary skill in the art will recognize that various changes and modifications of the embodiments described herein can be made without departing from the scope and spirit of the disclosure. Also, descriptions of well-known functions and constructions are omitted for clarity and conciseness.

Exemplary embodiments of the present disclosure provide caps that can reduce the number of device types and logistics currently needed in the hospital setting for connecting, capping, and/or disinfecting male and female threaded fluid Luer connectors, by roughly half by including in a single cap or device features allowing it to be use with both male and female threaded fittings.

In an exemplary implementation of the embodiments of present disclosure, a cap, connector cap or disinfecting cap includes integrated thread, or threads, and other features in any and all combinations allowing it to interface with both male and female threaded fittings. Male threaded fittings are present on female Luer connectors. Female threaded fittings are present on male Luer connectors. The threads can be sufficient to interlock with a mating feature (such as one or more protrusions, lugs and/or thread) of a hub or tip of a needleless connector, as described for example in related U.S. patent application Ser. Nos. 15/408,278 and 15/408,187, both filed on Jan. 17, 2017.

According to yet further exemplary implementations of the embodiments of the present disclosure, both of the male and female threads coincide with each other on the inner and outer face of the threaded protrusion.

According to still further exemplary implementations of the embodiments of the present disclosure, female threads are sized and have a thread pattern that will engage with a standard ISO594-2 type of male fitting and/or a male threads that are sized and have a thread pattern that will engage with a standard ISO594-2 type of female fitting. An example of an ISO594-2 type of fitting is a Q-style fitting.

According to other further exemplary implementations of the embodiments of the present disclosure, the cap is compatible with ISO80369-7 connectors.

In one or more embodiments, the female connector may be selected from the group consisting essentially of needle-free connectors, catheter Luer connectors, stopcocks, and hemodialysis connectors. In one or more embodiments, the needleless connector is selected from a Q-Syte connector, MaxPlus, MaxPlus Clear, MaxZero, UltraSite, Caresite, InVision-Plus, Safeline, OneLink, V-Link, ClearLink, NeutraClear, Clave, MicroClave, MicroClave Clear, Neutron, NanoClave, Kendall, Nexus, InVision, Vadsite, Bionector, etc.

In one or more embodiments, the male connector may be an intravenous tubing end, a stopcock or male lock Luer.

The caps herein can achieve disinfection when used on Luer connectors by integrating a disinfection sponge in a cavity of the caps. The caps are designed to be compatible in interacting with various disinfectants. In one or more embodiments, the disinfectant of the disinfectant sponge may include variations of alcohol or chlorhexidine. In one or more embodiments, the disinfectant is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the disinfectant comprises at least one of chlorhexidine gluconate and chlorhexidine diacetate. In one or more embodiments, the disinfectant is a fluid or a gel.

In use, compression of the disinfection sponge towards a top wall of the cap housing upon connection to the female Luer connector or the male Luer connector allows the connector to contact the disinfectant to disinfect the female Luer connector or the male Luer connector.

Before describing several exemplary embodiments of the disclosure, it is to be understood that the disclosure is not limited to the details of construction or process steps set forth in the following description. The disclosure is capable of other embodiments and of being practiced or being carried out in various ways.

Referring now to the drawings, wherein like reference numerals designate identical or corresponding parts throughout the several views, embodiments of the present disclosure are described as follows.

Turning to the figures, FIG. 1 is a perspective side view of an exemplary medical assembly 20 according to an embodiment, wherein a cap 5 according to any embodiment disclosed herein is attached to a medical connector 10, which is attached to, for example, tubing 15. The caps herein are suitable for attaching to both male and/or female medical connectors. The male and/or female connectors in turn are used to connect to medical devices such as catheters and tubing.

Figure 2:
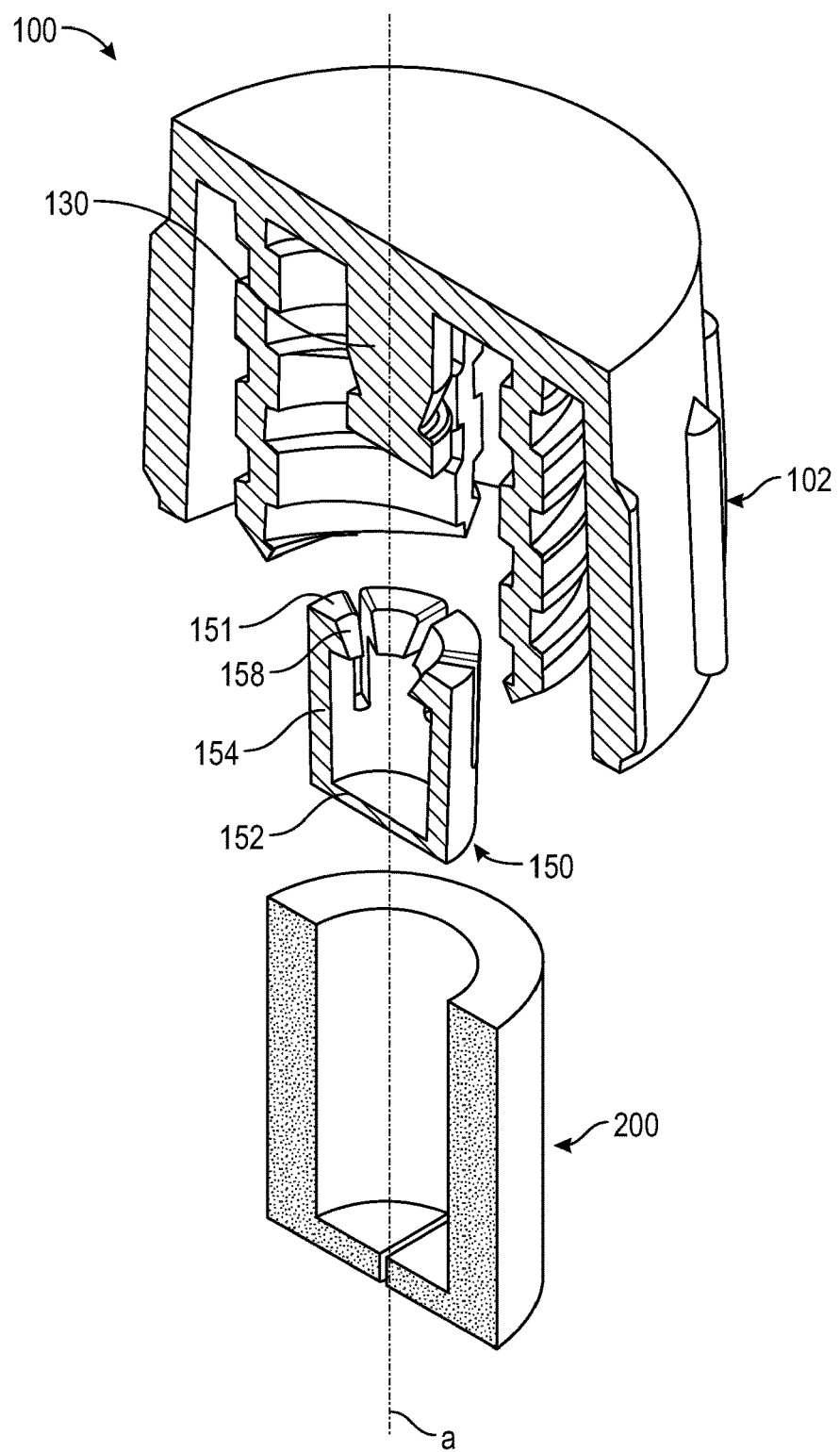
FIG. 2 illustrates an exploded cross-sectional perspective top view of an exemplary cap according to an embodiment.

In FIG. 2, an exploded cross-sectional perspective top view along longitudinal axis "a" of an exemplary cap according to an embodiment is provided. A cap 100 comprises a housing 102, a protrusion 114, an elongate member 130, an insert 150, and a disinfection sponge 200. In this embodiment, a pressure seal is a combination of: the elongate member 130 and the insert 150, the insert 150 comprising a top edge 151 and a bottom wall 152, between which spans a sidewall 154 of the insert 150. The top edge 151 of the insert 150 comprises an inside surface 158. The insert 150 engages with the elongate member 130 along the inside surface 158 of the top edge 151. In one or more embodiments, the insert 150 snap-fits onto the elongate member 130. Upon assembly, the insert 150 resides in a hollow 206 defined by the disinfection sponge 200.

Figure 3:
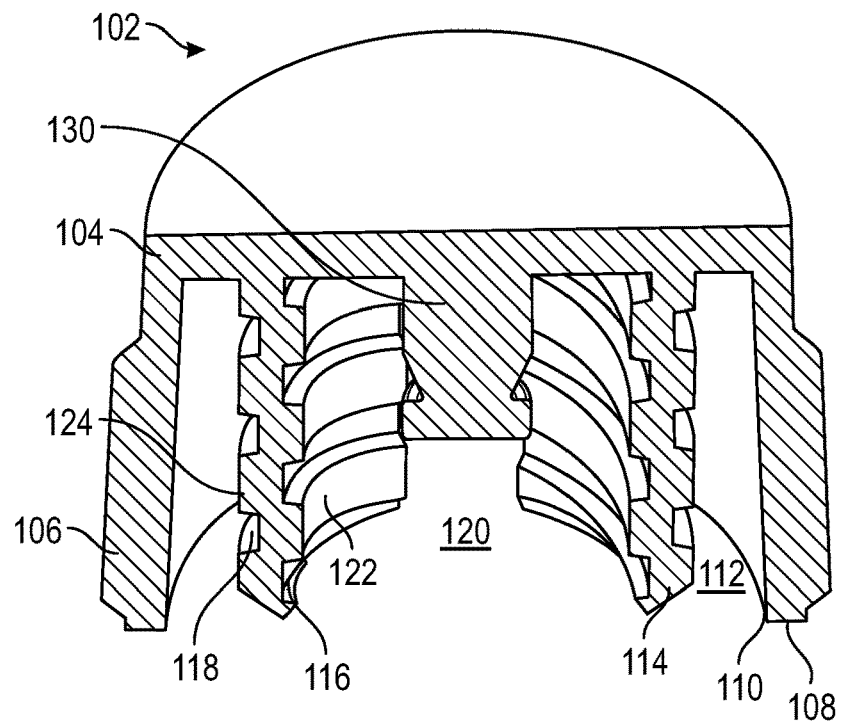
FIG. 3 illustrates a cross-sectional perspective top view of a housing according to an exemplary embodiment.

Shown in a cross-sectional perspective top view in FIG. 3, the housing 102 comprises a top wall 104, a sidewall 106, a protrusion 114, and an elongate member 130. The sidewall 106 is essentially cylindrical. The sidewall 106 defines a first cavity 112 and an open bottom 108, the open bottom 108 defining opening 110. The elongate member 130 extends from a first end 138 attached to an inside surface of the top wall 104 of the housing 102 to a second end 140. The protrusion 114 is positioned within the first cavity 112 and can be essentially cylindrical and coaxial with the sidewall 106. The opening 110 is disposed at the open bottom 108 of the housing 102. An inner surface of the top wall 104 can form a top of cavity 112. In an embodiment, the protrusion 114 is integrally formed with the housing 102. In another embodiment, the protrusion 114 is attached to the top wall 104 of the housing 102 by, for example, a snap-fit attachment. A second cavity 120 of the housing 102 is defined by an inner surface 116 of the protrusion 114. The inner surface 116 includes inner threads 122. The protrusion 114 also has an outer surface 118, including outer threads 124. In one or more embodiments, the inner threads 122 have a size and pitch to engage a threaded fitting of a female connector, such as for example, a female Luer connector. Such connectors are generally and commonly used as catheter and other fluid-tight protective connectors in medical applications. The inner threads 122 are sufficient to interlock with a mating feature of the female needleless connector such as a threaded fitting with male threads. The outer threads 124 are sufficient to interlock with a mating feature of a male needleless connector such as a threaded fitting with female threads. In one or more embodiments, the protrusion 114 can include one or more cantilevered prongs separated by one or more respective gaps. In one or more embodiments, at least one of the prongs can be configured to bend to facilitate interference fit between the protrusion and the mating feature of a male needleless connector or female needleless connector. In one or more embodiments, protrusion 114 can extend essentially from an inner surface of the top wall 104 toward the open bottom 108 of the housing 102. In one or more embodiments, the protrusion 114 can extend essentially parallel to the sidewall 106 of the housing.

Figure 4:
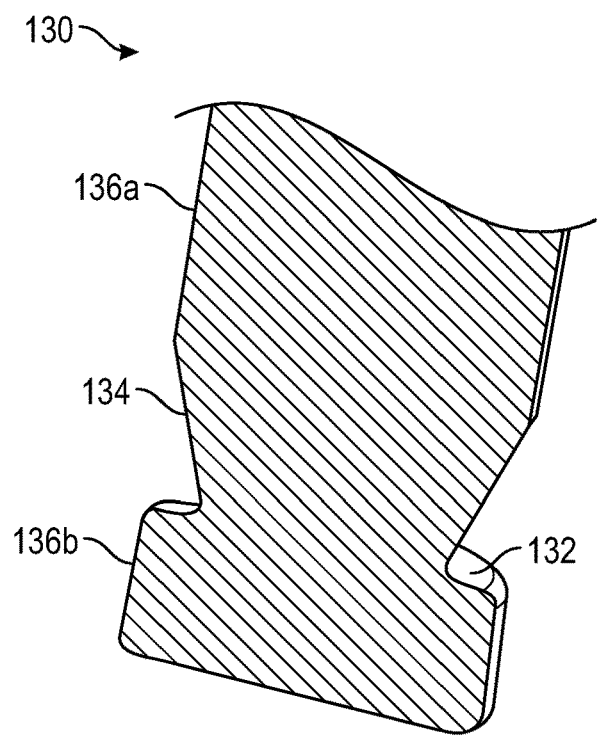
FIG. 4 illustrates a partial cross-sectional view of the elongate member of FIG. 3.

In FIG. 4, a partial cross-sectional view of the elongate member 130 shows an upper sliding section 136a, which extends from the first end 138 (not shown) continuing into an inward tapered slanted section 134. The slanted section 134 ends to meet a shoulder section 132 of the elongate member 130. At the second end 140 of the elongate member 130 is a lower sliding section 136b. An insert slidably engages with the elongate member 130.

Figure 5:
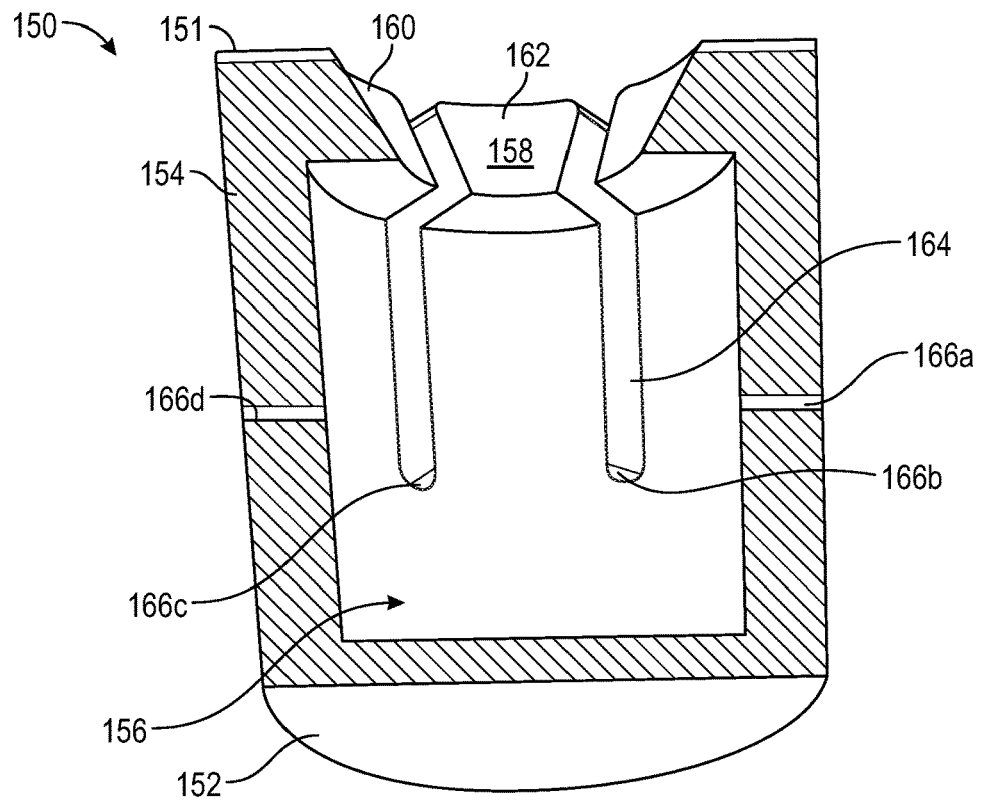
FIG. 5 illustrates a cross-sectional view of an insert according to according to an embodiment.
Figure 6:
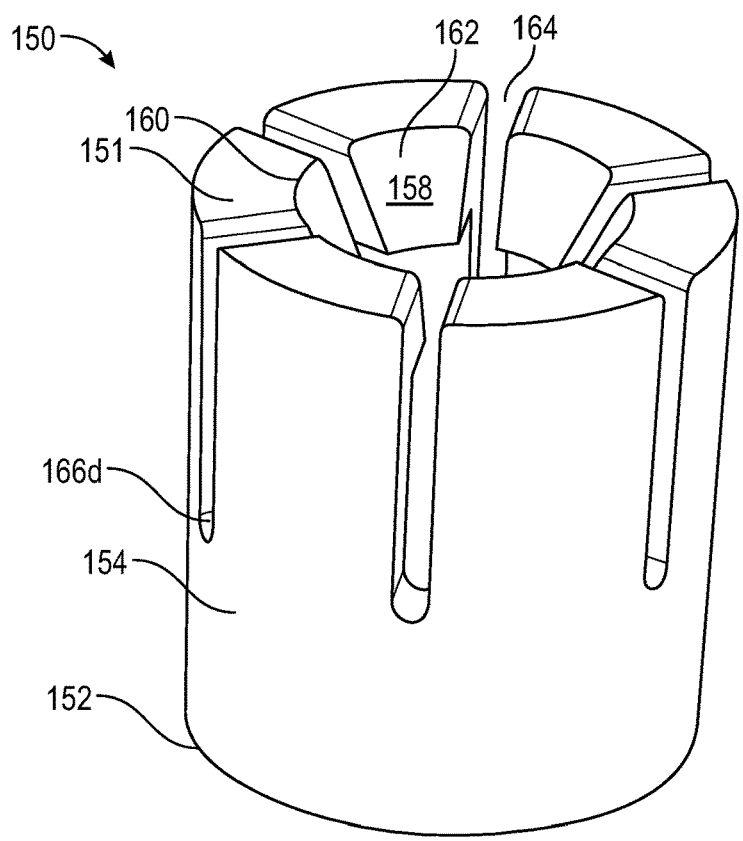
FIG. 6 illustrates a perspective top view of the insert of FIG. 5.

FIG. 5 provides a cross-sectional view and FIG. 6 provides a perspective top view of the insert 150 according to according to an embodiment. The insert 150, which may be referred to as a slidable insert, comprises a substantially cylindrical body having the bottom wall 152, which is closed, and the top edge 151, which is open, between which spans the sidewall 154. The top edge 151 radially hangs over the insert sidewall 154 defining an aperture 160. The sidewall 154 defines a chamber 156 within the insert. A plurality of slits 164 exists radially around the top edge 151, which define multiple prongs 162 around top edge 151 of the insert 150. The faces 158 of the prongs 162 are chamfered from the top edge 151 of the insert 150. The prongs 162 have bottom ends defined by where each slit ends 166a, 166b, 166c, 166d. The slits 164 provide flexibility to each prong 162, allowing the insert 150 to slide along an elongate member (e.g., item 130 of FIGS. 2-3) when a force along the central axis (e.g., "a" of FIG. 2) is applied, such as when a needleless connector or IV tubing end is attached to the cap. The insert can be made of plastic, or a thermoplastic elastomer (TPE), or a blend of plastic (such as polypropylene (PP) or polyethylene (PE)) with TPE material. The insert is suitable for universal disinfecting caps to be used on, for example, both needleless connectors and stopcocks.

The pressure seal comprising an elongate member and insert can be included in caps that are not unisex as well, including but not limited to female disinfecting caps such as BD PureHub™. The pressure seal would permit the female disinfecting caps to be used with stopcocks. In an embodiment, a cap comprises: a housing comprising: a top wall; an essentially cylindrical sidewall forming a first cavity; and an open bottom formed by the cylindrical sidewall with an opening to the first cavity within the housing for receiving a hub of a medical connector; and an inner thread on an inner surface of the cylindrical sidewall, the inner thread being sufficient to interlock with a threaded fitting of a medical connector; a disinfection sponge configured within the first cavity; and an elongate member attached to the housing, and an insert slidably engaged with the elongate member and disposed adjacent to a surface of the disinfection sponge.

Figure 7:
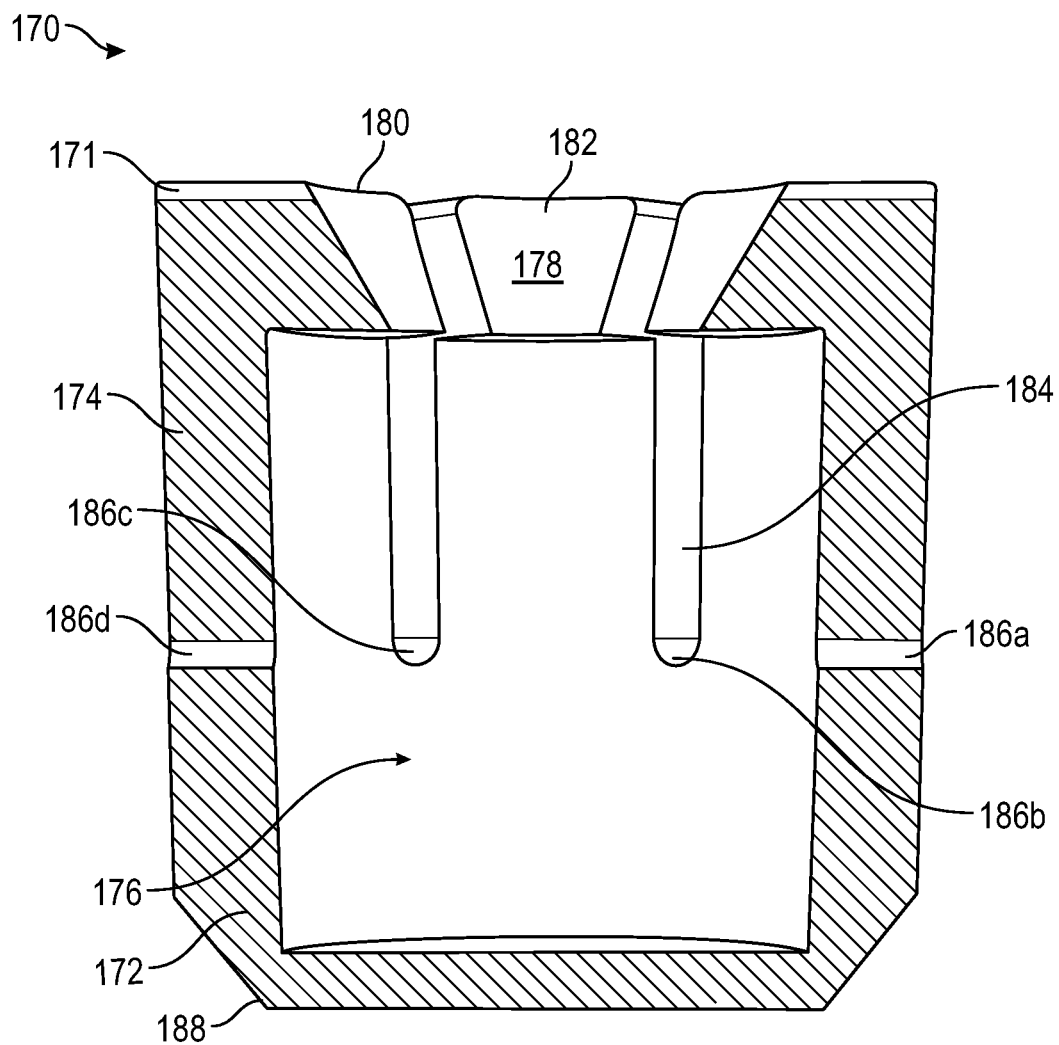
FIG. 7 illustrates a cross-sectional side view of an insert according to another embodiment.

FIG. 7 provides a cross-sectional view an insert 170 according to according to another embodiment, which comprises a tapered edge. The insert 170, which may be referred to as a slidable insert, comprises a substantially cylindrical body having a bottom wall 172, which is closed, and a top edge 171, which is open, between which spans a sidewall 174. The top edge 171 radially hangs over the insert sidewall 174 defining an aperture 180. The sidewall 174 defines a chamber 176 within the insert. A plurality of slits 184 exists radially around the top edge 171, which define multiple prongs 182 around top edge 171 of the insert 170. The faces 178 of the prongs 182 are chamfered from the top edge 171 of the insert 170. The prongs 182 have bottom ends defined by where each slit ends 186a, 186b, 186c, 186d. The bottom wall 172 further comprises a tapered edge 188, which may be configured to complement a connector and/or medical device for creating sealed contact. In one or more embodiments, the external geometry of the insert 150 has the tapered edge 188 with a range of angles that can be sufficiently complementary to a Luer taper. When the insert engages with an open lumen of a medical Luer connector such as a catheter or stopcock, the complementary inner Luer wall applies radial pressure on the insert to make the snap fit tighter and prevent insert from moving along central axis even when subject to a force along the central axis.

Figure 8:
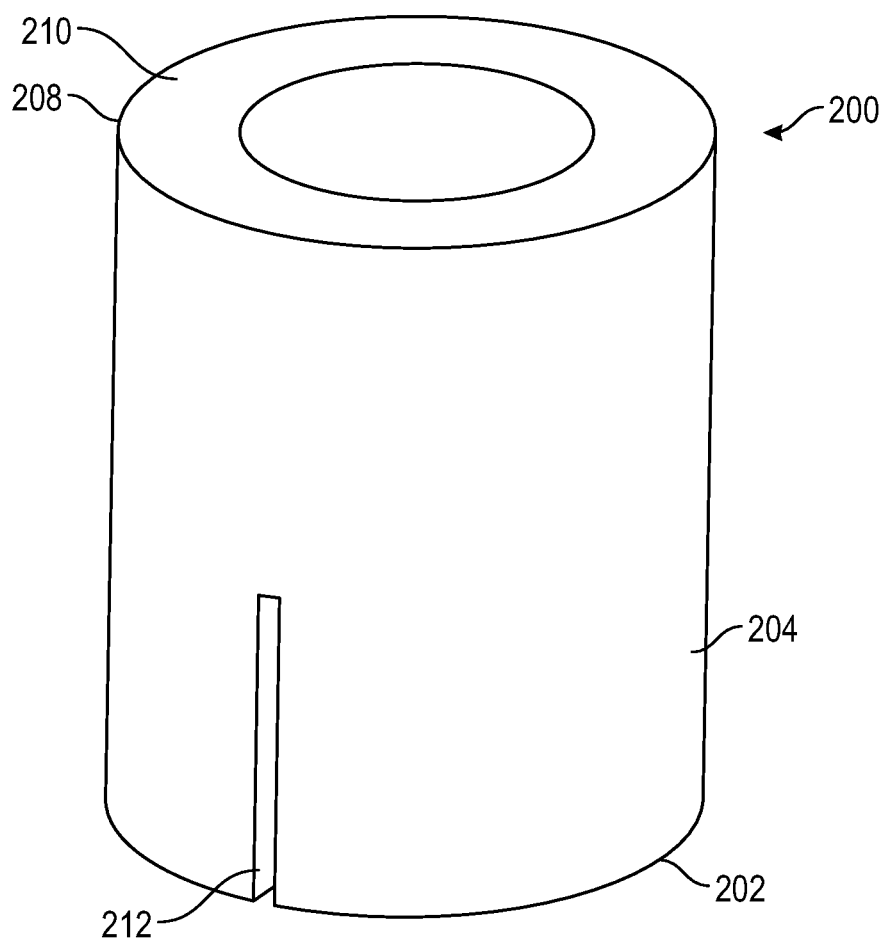
FIG. 8 illustrates a perspective top view of an disinfection sponge according to an embodiment.
Figure 9:
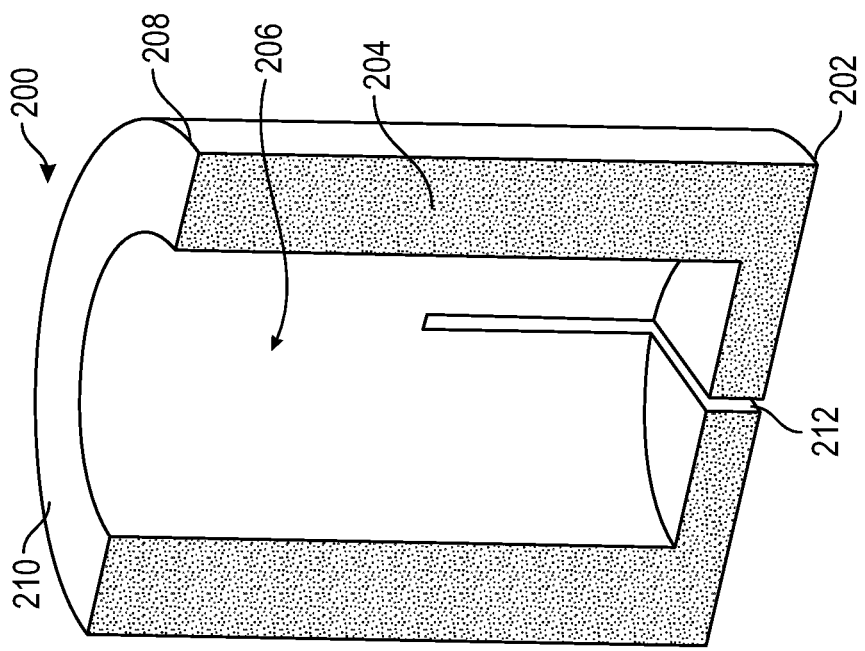
FIG. 9 illustrates a cross-sectional perspective top view of the disinfection sponge of FIG. 8.

The caps of the disclosure comprise a disinfectant sponge, which allows a practitioner to streamline the disinfecting process. FIG. 8 provides a perspective top view and FIG. 9 provides a cross-sectional perspective top view of a disinfection sponge, which is substantially symmetrical, according to an embodiment. A disinfection sponge 200 has a generally cylindrical body with sidewall 204 spanning between a slotted end 202 and an open end 208 having an end wall 210. In the embodiment of FIGS. 8-9, slot 212 extends into opposing portions of the sidewall 204 through a diameter of the slotted end 202. In one or more embodiments, the slot 212 extends less than about halfway along the sidewall 204. The sidewall 204 defines a hollow 206. The slot allows, for example, a Luer tip of a male Luer connector to be inserted in the hollow cylinder cavity so the sponge side wall can interact with a side surface of the male Luer connector and release the disinfectant onto a Luer surface. The slot opens when the male Luer connector is threaded onto the cap and the Luer opens up the slot by pushing both sides of the sponge away.

Figure 10:
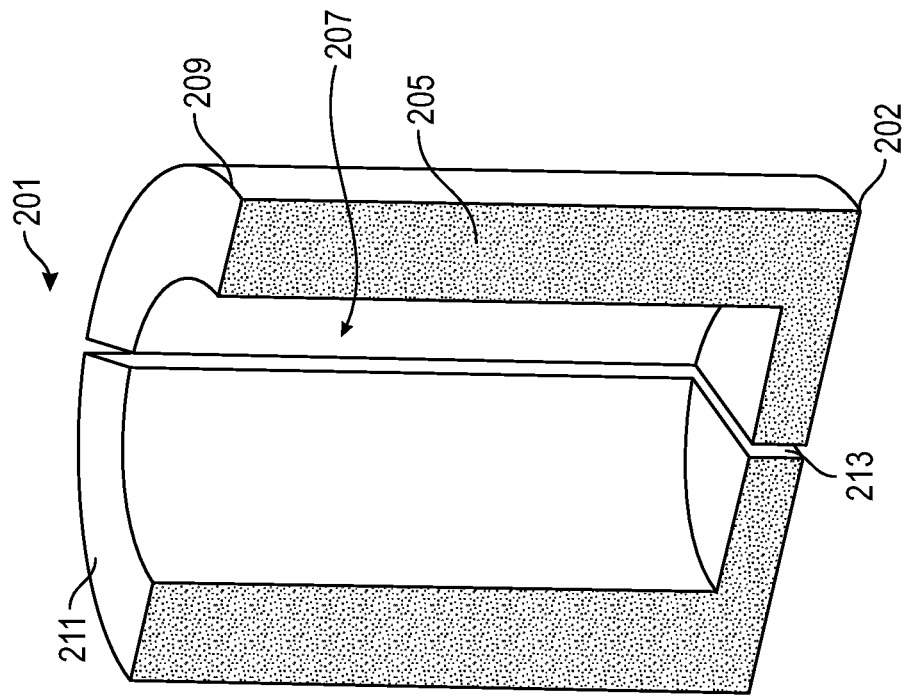
FIG. 10 illustrates a cross-sectional perspective top view of a disinfection sponge according to another embodiment.

FIG. 10 provides a cross-sectional perspective top view of a disinfection sponge, which is substantially symmetrical, according to another embodiment. A disinfection sponge 201 has a generally cylindrical body with sidewall 205 spanning between a slotted end 202 and an open end 209 having an end wall 211. In the embodiment of FIG. 10, slot 213 extends from the end wall 311 along the sidewall 205 through a diameter of the slotted end 202. The sidewall 205 defines a hollow 207. As needed, in one or more embodiments, the slots may have intermittent connections between portions of the sidewall 205 so that the sponge is a single piece for handling. The slot allows, for example, a Luer tip of a male Luer connector to be inserted in the hollow cylinder cavity so the sponge side wall can interact with a side surface of the male Luer connector and release the disinfectant onto a Luer surface. The slot opens when the male Luer connector is threaded onto the cap and the Luer opens up the slot by pushing both sides of the sponge away.

Figure 11:
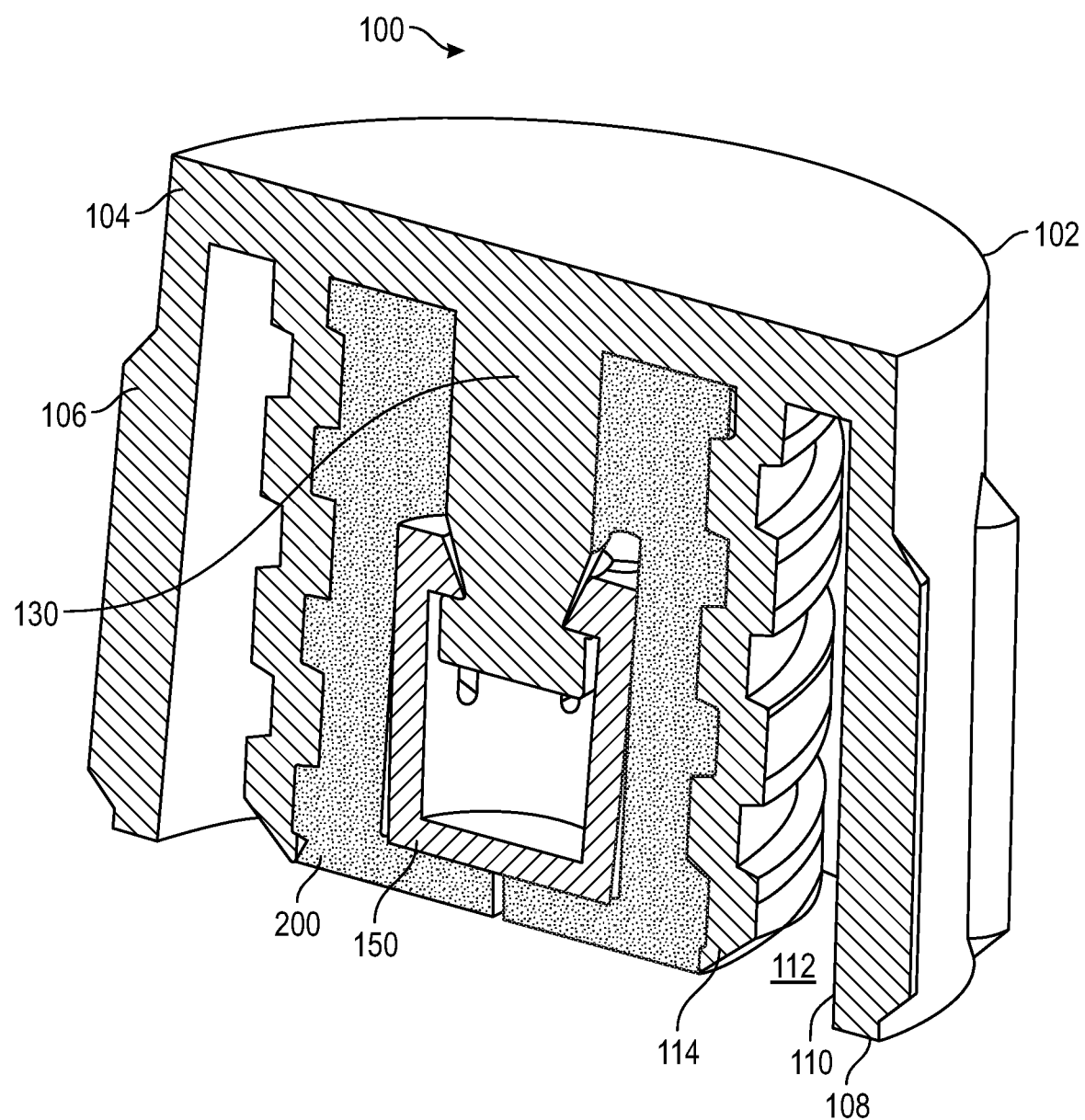
FIG. 11 diagrammatically illustrates a cross-sectional perspective top view of the cap according to FIG. 2.

FIG. 11 diagrammatically illustrates a cross-sectional perspective top view of the cap according to FIG. 2 in assembled form. The cap 100 comprises the housing 102, the top wall 104, the sidewall 106, the open bottom 108 defining the opening 110, the protrusion 114, and the elongate member 130 is shown with the insert 150 snap-fit into position. The insert 150 resides in a hollow defined by the disinfection sponge 200, which in turn resides in the cavity defined by the inner surface of the protrusion 114. The sidewall 106 defines a cavity 112, which is available for receipt of a hub of a connector. In one or more embodiments, upon assembly, the disinfection sponge 200 is in direct contact with an interior surface of the top wall 104.

In an exemplary implementation, a peel seal can be provided to seal the opening 110 prior to use of cap 100, for example, by attachment to a surface of a rim of the open bottom 108 of housing 102. In one or more embodiments, the peelable seal comprises an aluminum or multi-layer polymer film peel back top. In a specific embodiment, the peelable seal is heat-sealed or induction sealed to the open end of the cap. In one or more embodiments, the peelable seal comprises a moisture barrier. According to exemplary embodiments of the disclosure, the cap 100 can receive a tip or hub of a needleless connector, for example after the peel seal sealing cavity is removed or when the peal sealing film is pierced, within the cavity 112 and secure, for example, threadedly, the tip of the needleless connector within the cavity 112.

Figure 12:
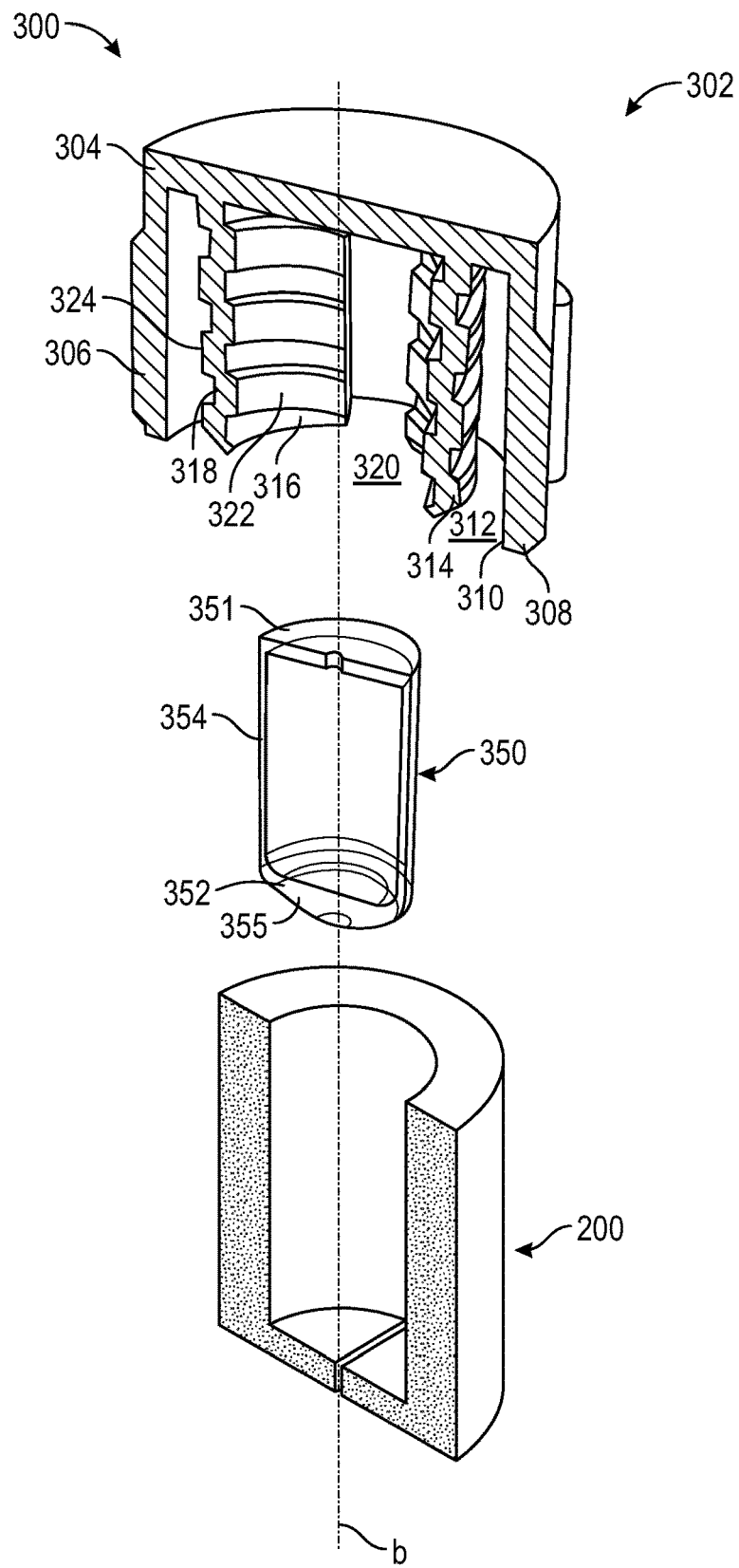
FIG. 12 illustrates an exploded cross-sectional perspective top view of an exemplary cap according to an embodiment.

In FIG. 12, an exploded cross-sectional perspective top view along longitudinal axis "b" of an exemplary cap according to an embodiment is provided. A cap 300 comprises a housing 302, a top wall 304, a sidewall 306 that is substantially cylindrical, and a protrusion 314. The sidewall 306 is essentially cylindrical. The sidewall 306 defines a first cavity 312 and an open bottom 308, the open bottom 308 defining opening 310. The protrusion 314 is positioned within the first cavity 312 and can be essentially cylindrical and coaxial with the sidewall 306. The opening 310 is disposed at the open bottom 308 of the housing 302. An inner surface of the top wall 304 can form a top of cavity 312. In an embodiment, the protrusion 314 is integrally formed with the housing 302. In another embodiment, the protrusion 314 is attached to the top wall 304 of the housing 302 by, for example, a snap-fit attachment. A second cavity 320 of the housing 302 is defined by an inner surface 316 of the protrusion 314. The inner surface 316 includes inner threads 322. The protrusion 314 also has an outer surface 318, including outer threads 324. In one or more embodiments, the inner threads 322 have a size and pitch to engage a threaded fitting of a female connector, such as for example, a female Luer connector. Such connectors are generally and commonly used as catheter and other fluid-tight protective connectors in medical applications. The inner threads 322 are sufficient to interlock with a mating feature of the female needleless connector such as a threaded fitting with male threads. The outer threads 324 are sufficient to interlock with a mating feature of a male needleless connector such as a threaded fitting with female threads. In one or more embodiments, the protrusion 314 can include one or more cantilevered prongs separated by one or more respective gaps. In one or more embodiments, at least one of the prongs can be configured to bend to facilitate interference fit between the protrusion and the mating feature of a male needleless connector or female needleless connector. In one or more embodiments, protrusion 314 can extend essentially from an inner surface of the top wall 304 toward the open bottom 308 of the housing 302. In one or more embodiments, the protrusion 314 can extend essentially parallel to the sidewall 306 of the housing.

In this embodiment, a pressure seal is a flexible insert 350 comprising a top edge 351 and a bottom wall 352, between which spans a sidewall 354 of the flexible insert 350. The bottom wall 352 of the flexible insert 350 comprises a tapered surface 355. Upon assembly, the insert 350 resides in a hollow 206 defined by disinfection sponge 200. In one or more embodiments, the flexible insert is disposed entirely in the hollow when in an uncompressed state.

Figure 13:
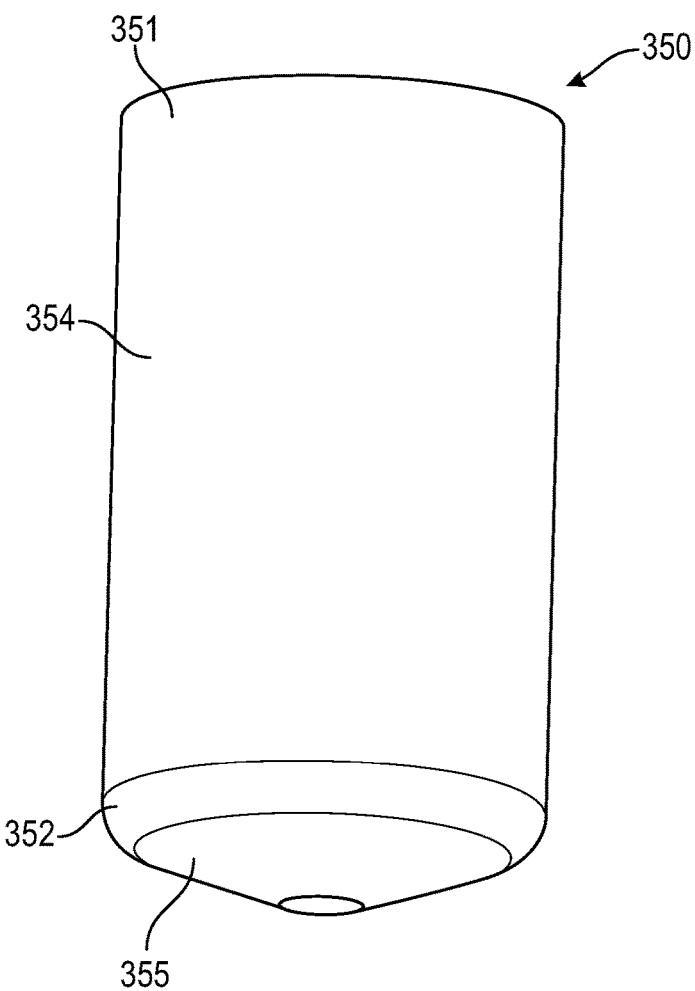
FIG. 13 illustrates a perspective bottom view of a flexible insert according to an embodiment.
Figure 14:
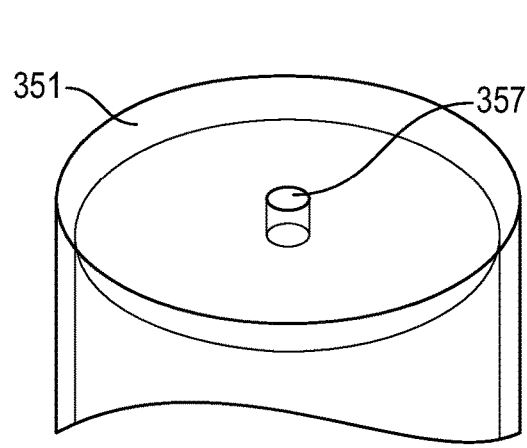
FIG. 14 illustrates a partial perspective top view of a flexible insert according to another embodiment.
Figure 15:
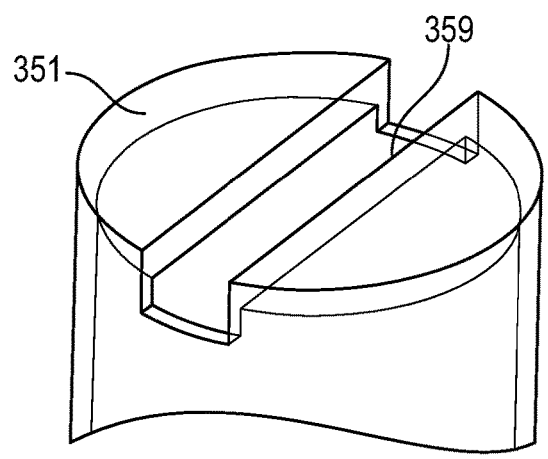
FIG. 15 illustrates a partial perspective top view of an flexible insert according to another embodiment.

FIG. 13 provides a perspective bottom view of the flexible insert 350 according to according to an embodiment. The flexible insert 350 comprises a substantially cylindrical body having the bottom wall 352, which is closed and has the tapered surface 355, and the top edge 351 between which spans the sidewall 354. The top edge 351 may be configured to fit to cap designs as desired. In one or more embodiments, the flexible insert 350 attaches to the top wall of the housing (e.g., item 304 of FIG. 12). In FIG. 14, the top edge 351 of the flexible insert 350 comprises an attachment feature 357 for attaching to an inside surface of a top wall of a housing of a cap. In FIG. 14, the attachment feature 357 is an opening in a center of the top wall 351. In FIG. 15, the top edge 351 comprises an attachment feature 359, which is a channel through a diameter of the top wall 351.

The external geometry of the flexible insert 350 is sufficiently complementary to open lumen Luer connectors for engaging. When the flexible insert 350 engages with an open lumen in Luer connectors such as a catheter or stopcock, the complementary inner Luer wall applies radial pressure on the insert to make an interference fit. The flexible insert 350 may define a cavity chamber inside the insert. Walls of the flexible insert 350 maybe breathable and/or porous, which may provide a channel, orifice or air path to connect the inside chamber to outside of the chamber of the insert to allow compression.

The flexible insert may be a solid material that is soft to compress longitudinally so when the cap is attached to male and closed female Luer connectors such as needleless connectors and IV tubing end, it may retract toward a top wall at a closed end of cap housing, but rigid enough radially so it can form enough interference with open Luer such as catheters or stopcocks.

The pressure seal comprising a flexible insert can be included in caps that are not unisex as well, including but not limited to female disinfecting caps such as BD PureHub™. The pressure seal would permit the female disinfecting caps to be used with stopcocks. In an embodiment, a cap comprises: a housing comprising: a top wall; an essentially cylindrical sidewall forming a first cavity; and an open bottom formed by the cylindrical sidewall with an opening to the first cavity within the housing for receiving a hub of a medical connector; and an inner thread on an inner surface of the cylindrical sidewall, the inner thread being sufficient to interlock with a threaded fitting of a medical connector; a disinfection sponge configured within the first cavity; and a flexible insert attached to the housing and disposed adjacent to a surface of the disinfection sponge.

Figure 16:
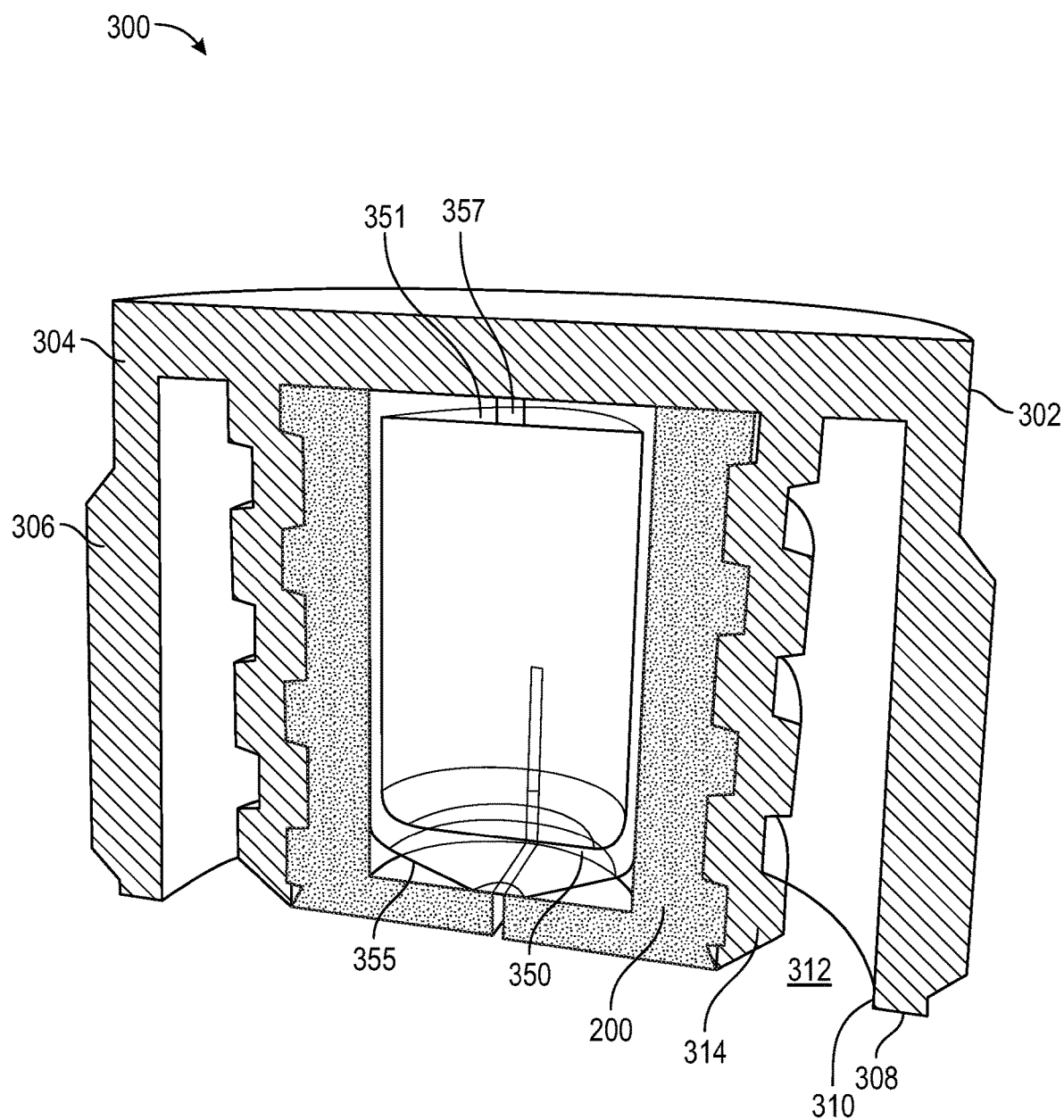
FIG. 16 diagrammatically illustrates a cross-sectional perspective top view of the cap according to FIG. 12.

FIG. 16 diagrammatically illustrates a cross-sectional perspective top view of the cap according to FIG. 12 in assembled form. The cap 300 comprising the housing 302, the top call 304, the sidewall 306, the open bottom 808 defining the opening 310, is shown with the flexible insert 350 in position. The flexible insert 350 resides in a hollow defined by the disinfection sponge 200, which in turn resides in the cavity defined by the inner surface of the protrusion 314. The sidewall 306 defines a cavity 312, which is available for receipt of a hub of a connector. In one or more embodiments, upon assembly, the disinfection sponge 200 is in direct contact with an interior surface of the top wall 304.

In an exemplary implementation, a peel seal can be provided to seal the opening 310 prior to use of cap 300, for example, by attachment to a surface of a rim of the open bottom 308 of housing 302. In one or more embodiments, the peelable seal comprises an aluminum or multi-layer polymer film peel back top. In a specific embodiment, the peelable seal is heat-sealed or induction sealed to the open end of the cap. In one or more embodiments, the peelable seal comprises a moisture barrier. According to exemplary embodiments of the disclosure, the cap 300 can receive a tip or hub of a needleless connector, for example after the peel seal sealing cavity is removed or when the peal sealing film is pierced, within the cavity 312 and secure, for example, threadedly, the tip of the needleless connector within the cavity 312.

Figure 17:
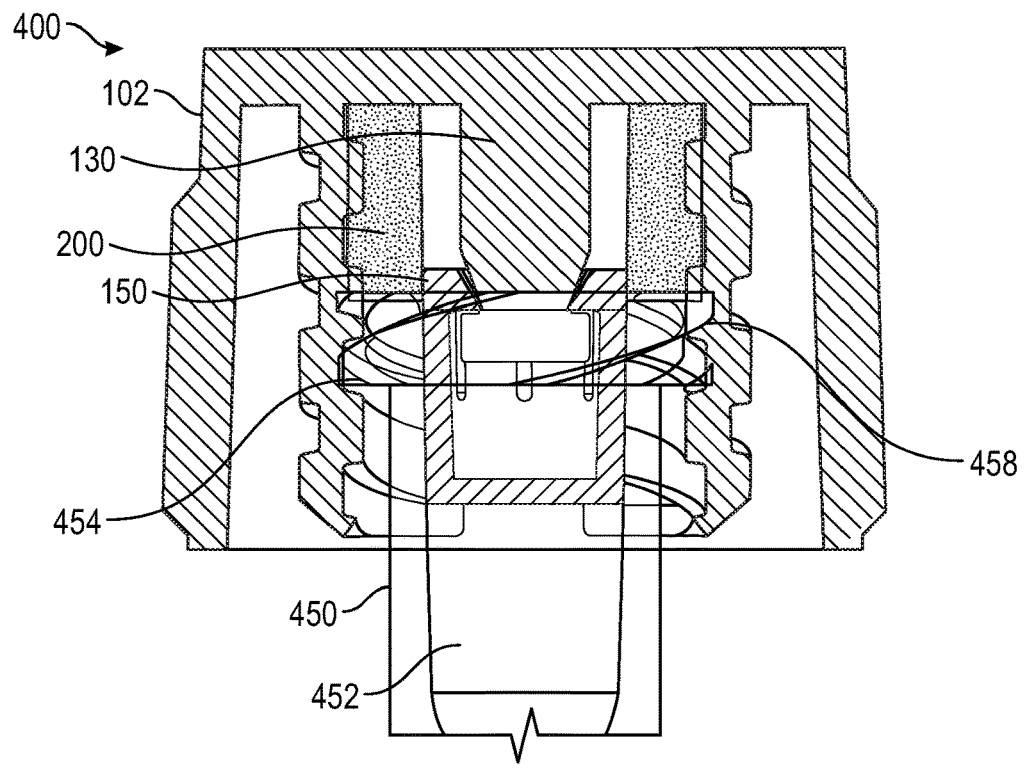
FIG. 17 illustrates an exemplary assembly showing a cap in a cross-section side view and a female medical connector in a partial side schematic view according to an embodiment.

FIG. 17 illustrates an exemplary assembly 400 of a cap 100 in a cross-section side view and a medical connector 450 in a partial side schematic view according to an embodiment. The cap 100 comprises the housing 102, the protrusion 114, the elongate member 130, the insert 150 snap fit and slidably engaged with the elongate member 130, and the disinfection sponge 200. The connector 450 is a female medical connector with an open female Luer port, which may be, for example, a needleless connector such as a catheter or stopcock, comprising an open lumen 452, a lumen edge 454, and male threaded fitting 458. The male threaded fitting 458 of the connector 450 engages with the inner threads 122 of the inner surface of the protrusion 114. When the insert 150 engages with the open lumen 452, a complementary inner wall, e.g. Luer wall, applies radial pressure on the insert 150 to make the snap fit tighter by bending prongs on the insert inward towards the central axis, and preventing insert from moving along central axis even when subject to a force along the central axis. The lumen edge 454 pushes the sponge 200 toward the top wall 104 at a closed end of the housing 102, allowing disinfectant to be dispensed onto the lumen edge 454. The insert 150 inhibits and/or prevents disinfectant from ingressing into the lumen 452. Also the insert can hold high pressure to avoid fluid leakage when, for example, a valve of a stopcock is not closed properly. In one or more embodiments, cap 400 provides a protective cover for a female Luer connector when engaged with the connector when a threaded fitting from the female Luer connector engages and forms a releasable connection with the inner threads 122 of cap 400.

Figure 18:
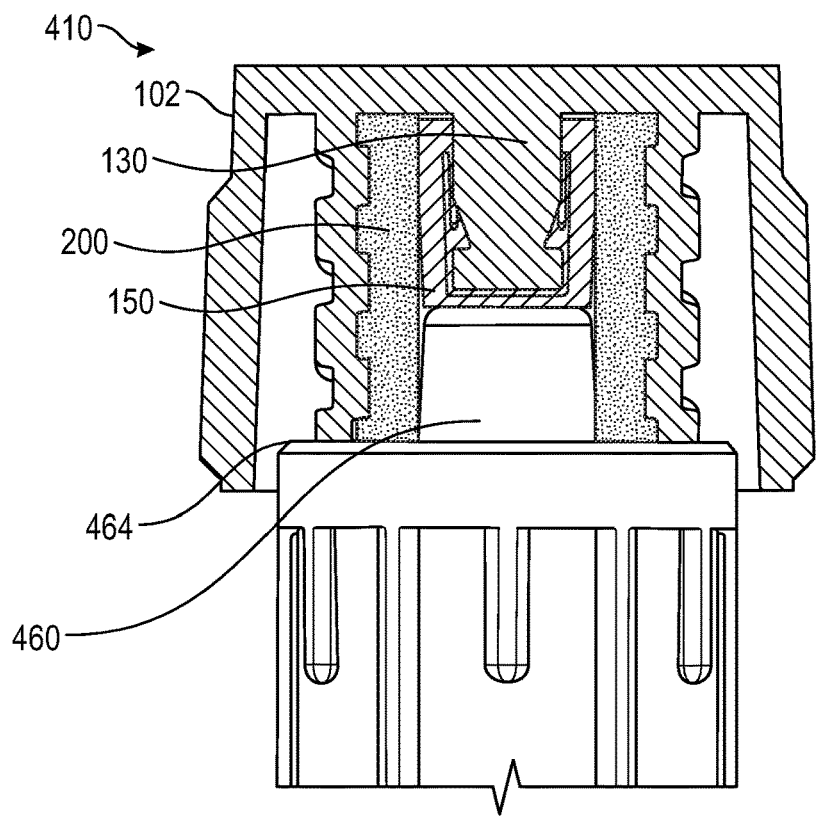
FIG. 18 illustrates an exemplary assembly showing a cap in a cross-section side view and a male connector in a partial schematic view according to an embodiment.

FIG. 18 illustrates an exemplary assembly 410 showing a cap 100 in a cross-section side view and a medical connector 460 in a partial schematic view according to an embodiment. The cap 100 comprises the housing 102, the protrusion 114, the elongate member 130, the insert 150 snap fit and slidably engaged with the elongate member 130, and the disinfection sponge 200. The connector 460 is a male medical connector, which may be, for example, an IV tubing end, comprising an open lumen 462, an edge 464, and a female threaded fitting 468. The female threaded fitting 468 of the connector 460 engages with the outer threads 124 of the inner surface of the protrusion 114. When the insert 150 engages with the edge 464, the prongs on the insert 150 expand radially outward to allow the insert 150 to move along the elongate member 130 and retract to top wall 104 at a closed end of the housing 102. The edge 464 pushes the sponge 200 toward the top wall 104 at a closed end of the housing 102, allowing disinfectant to be dispensed onto the lumen edge 464. The insert 150 inhibits and/or prevents disinfectant from ingressing into the open lumen 462. The bottom surface of the insert 150 can cover the open lumen 462 of the Luer tip on the connector, thereby mitigating disinfectant ingress. The insert can provide a sealing function to hold pressure from the liquid in the central lumen and fluid path, preventing leakage. In one or more embodiments, cap 410 provides a protective cover for a male Luer connector when engaged with the connector when a threaded fitting from the male Luer connector engages and forms a releasable connection with the inner threads 122 of cap 410.

Figure 19:
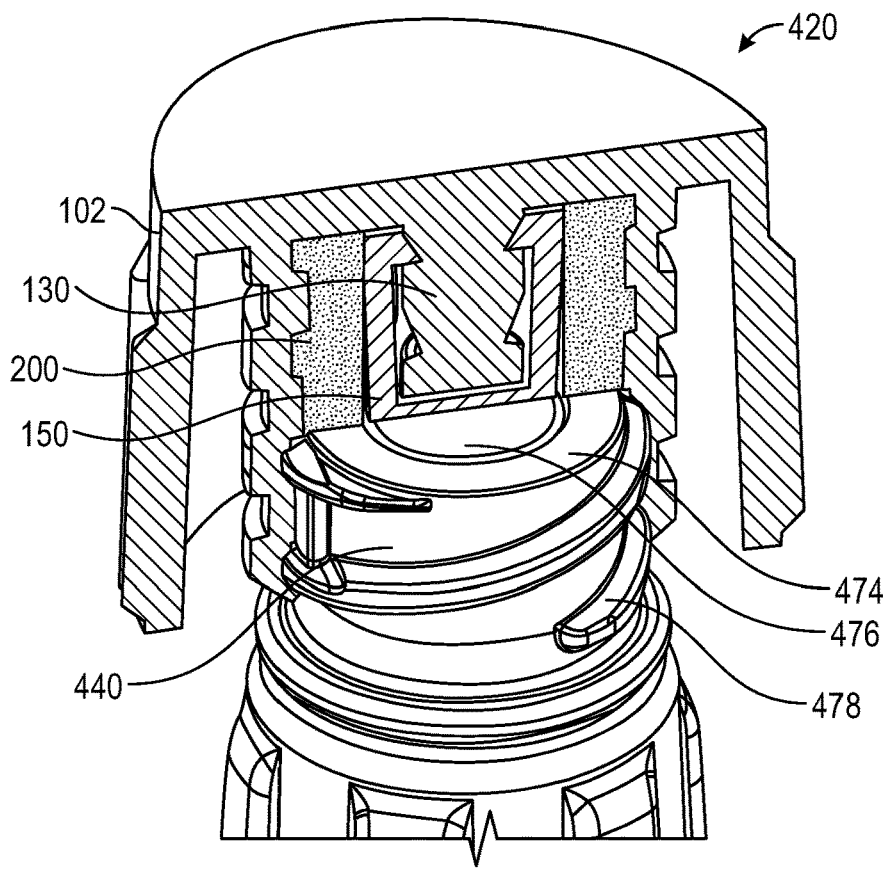
FIG. 19 illustrates an exemplary assembly showing a cap in a cross-section perspective top view and a female connector in a partial side perspective view according to an embodiment.

FIG. 19 illustrates an exemplary assembly 420 showing a cap 100 in a cross-section perspective top view and a medical connector 470 in a partial side perspective view according to an embodiment. The cap 100 comprises the housing 102, the protrusion 114, the elongate member 130, the insert 150 snap fit and slidably engaged with the elongate member 130, and the disinfection sponge 200. The connector 470 is a female medical needless connector, comprising a lumen edge 474, a septum 476, and male threaded fitting 478. Upon assembly, the male threaded fitting 478 of the connector 470 engages with the inner threads 122 of the inner surface of the protrusion 114. The lumen edge 474 pushes the sponge 200 toward the top wall 104 at a closed end of the housing 102, allowing disinfectant to be dispensed onto the lumen edge 474. When the cap 100 is attached to the needleless connector 470, the prongs on the insert 150 expand radially outward, to allow the insert 150 to move along the elongate member 130 and retract toward the top wall 104 at a closed end of the housing 102. This motion prevents the insert 150 from pushing on the septum 476 of the needleless connector 470, which avoids opening a fluid path and creating fluid leakage. In one or more embodiments, cap 420 provides a protective cover for a female needless connector when engaged with the connector when a threaded fitting from the female needleless connector engages and forms a releasable connection with the inner threads 122 of cap 420.

Figure 20:
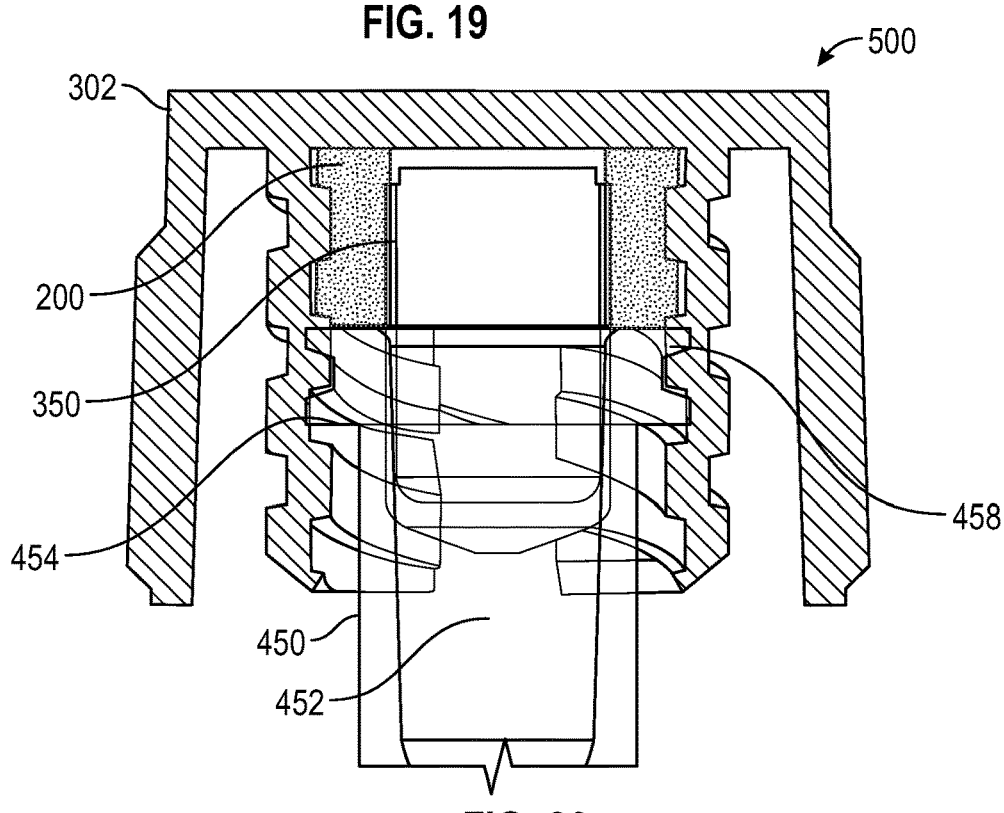
FIG. 20 illustrates an exemplary assembly showing a cap in a cross-section side view and a female medical connector in a partial side view according to an embodiment.

FIG. 20 illustrates an exemplary assembly 500 showing a cap 300 in a cross-section side view and a medical connector 450 in a partial side view according to an embodiment. The cap 300 comprises the housing 302, the protrusion 314, the flexible insert 350, and the disinfection sponge 200. The connector 450 is a female medical connector with an open female Luer port, which may be, for example, a needleless connector such as a catheter or stopcock, comprising an open lumen 452, a lumen edge 454, and male threaded fitting 458. The male threaded fitting 458 of the connector 450 engages with the inner threads 322 of the inner surface of the protrusion 314. When the insert 350 engages with the open lumen 452, a complementary inner wall, e.g. Luer wall, applies radial pressure on the insert 350 to make an interference fit with the inner wall. The lumen edge 454 pushes the sponge 200 toward the top wall 304 at a closed end of the housing 302, allowing disinfectant to be dispensed onto the lumen edge 454. The insert 350 inhibits and/or prevents disinfectant from ingressing into the lumen 452. Also the insert can hold high pressure to avoid fluid leakage when, for example, a valve of a stopcock is not closed properly. In one or more embodiments, cap 500 provides a protective cover for a female Luer connector when engaged with the connector when a threaded fitting from the female Luer connector engages and forms a releasable connection with the inner threads 322 of cap 500.

Figure 21:
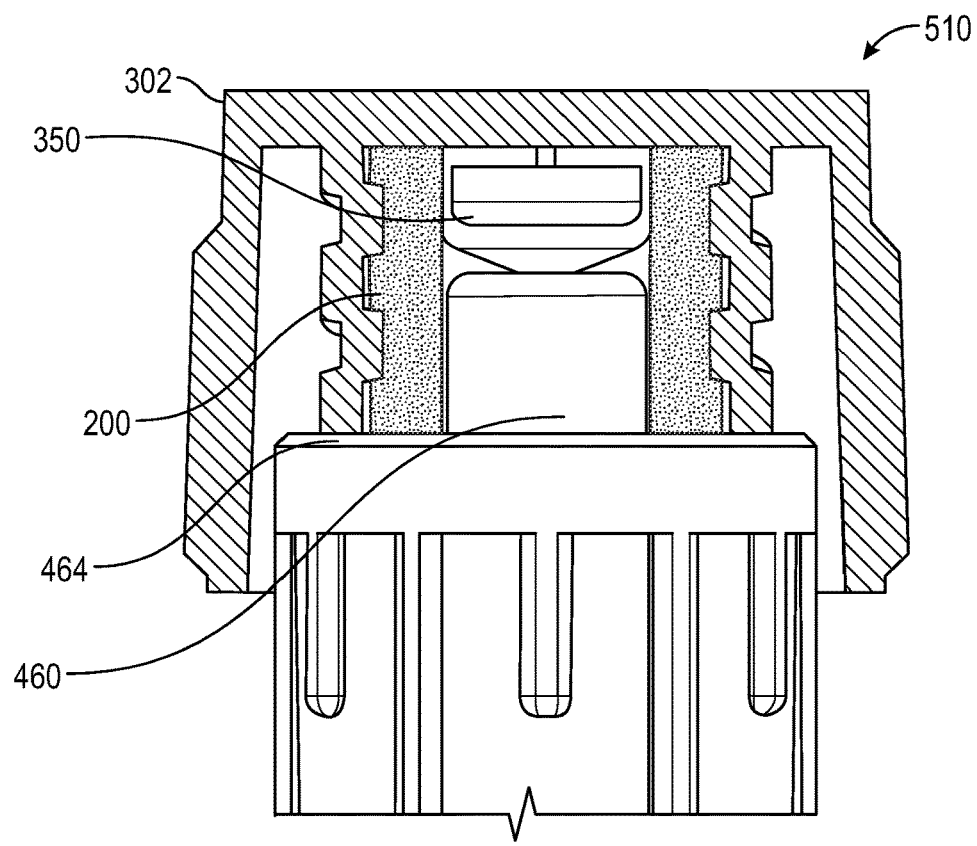
FIG. 21 illustrates an exemplary assembly showing a cap in a cross-section side view and a male connector in a partial schematic side view according to an embodiment.

FIG. 21 illustrates an exemplary assembly 510 showing a cap 300 in a cross-section side view and a medical connector 460 in a partial schematic side view according to an embodiment; and FIG. 18B illustrates a cross-section of the male connector of FIG. 21. The cap 300 comprises the housing 302, the protrusion 314, the insert 350, and the disinfection sponge 200. The connector 460 is a male medical connector, which may be, for example, an IV tubing end, comprising an open lumen 462, an edge 464, and a female threaded fitting 468. The female threaded fitting 468 of the connector 460 engages with the outer threads 324 of the inner surface of the protrusion 314. When the insert 350 engages with the open lumen 462, a complementary inner wall applies radial pressure on the insert 350 to make an interference fit with the inner wall. The edge 464 pushes the sponge 200 toward the top wall 304 at a closed end of the housing 302, allowing disinfectant to be dispensed onto the lumen edge 464. The insert 350 inhibits and/or prevents disinfectant from ingressing into the open lumen 462. The bottom surface of the insert 350 can cover the open lumen 462, thereby mitigating disinfectant ingress. The insert can provide a sealing function to hold pressure from the liquid in the central lumen and fluid path, preventing leakage.

Figure 22:
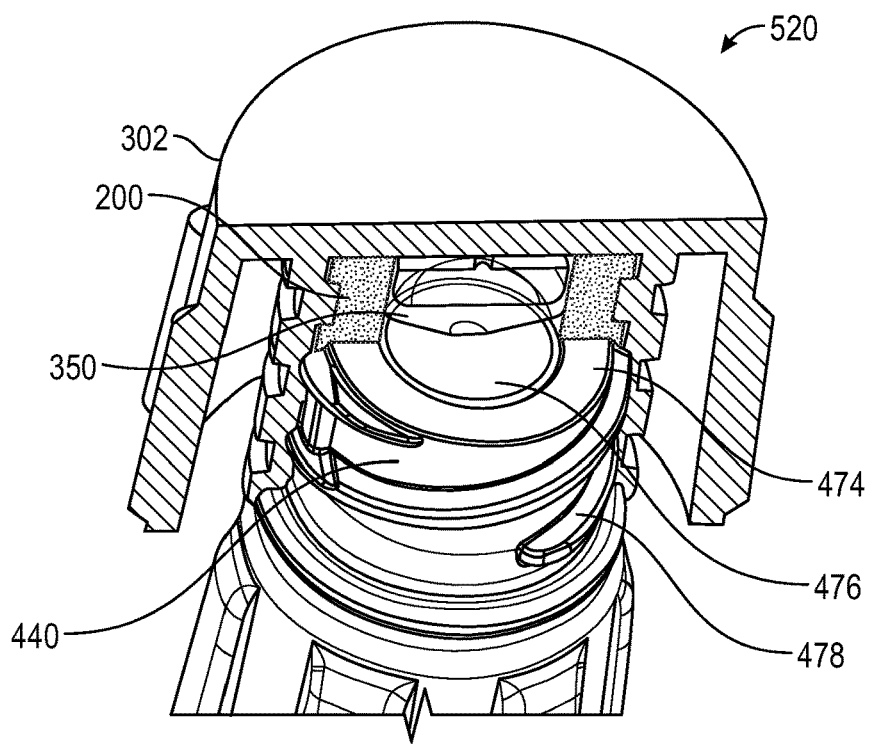
FIG. 22 illustrates an exemplary assembly showing a cap in a cross-section perspective top view and a female connector according to an embodiment FIG. 23 diagrammatically illustrates a cap in a cross-section side view according to an embodiment.

FIG. 22 illustrates an exemplary assembly 520 showing a cap 300 in a cross-section perspective top view and a medical connector 470 according to an embodiment. The cap 300 comprises the housing 302, the protrusion 314, the flexible insert 350, and the disinfection sponge 200. The connector 470 is a female medical needless connector, comprising a lumen edge 474, a septum 476, and male threaded fitting 478. Upon assembly, the male threaded fitting 478 of the connector 470 engages with the inner threads 322 of the inner surface of the protrusion 314. The lumen edge 474 pushes the sponge 200 toward the top wall 304 at a closed end of the housing 302, allowing disinfectant to be dispensed onto the lumen edge 474. When the insert 350 engages with the open lumen 452, a complementary inner wall, e.g. Luer wall, applies radial pressure on the insert 350 to make an interference fit with the inner wall. The insert 350 is compliant enough to that it does not push on the septum 476 of the needleless connector 470, which avoids opening a fluid path and creating fluid leakage. In one or more embodiments, cap 520 provides a protective cover for a female Luer connector when engaged with the connector when a threaded fitting from the female Luer connector engages and forms a releasable connection with the inner threads 322 of cap 520.

Figure 23:
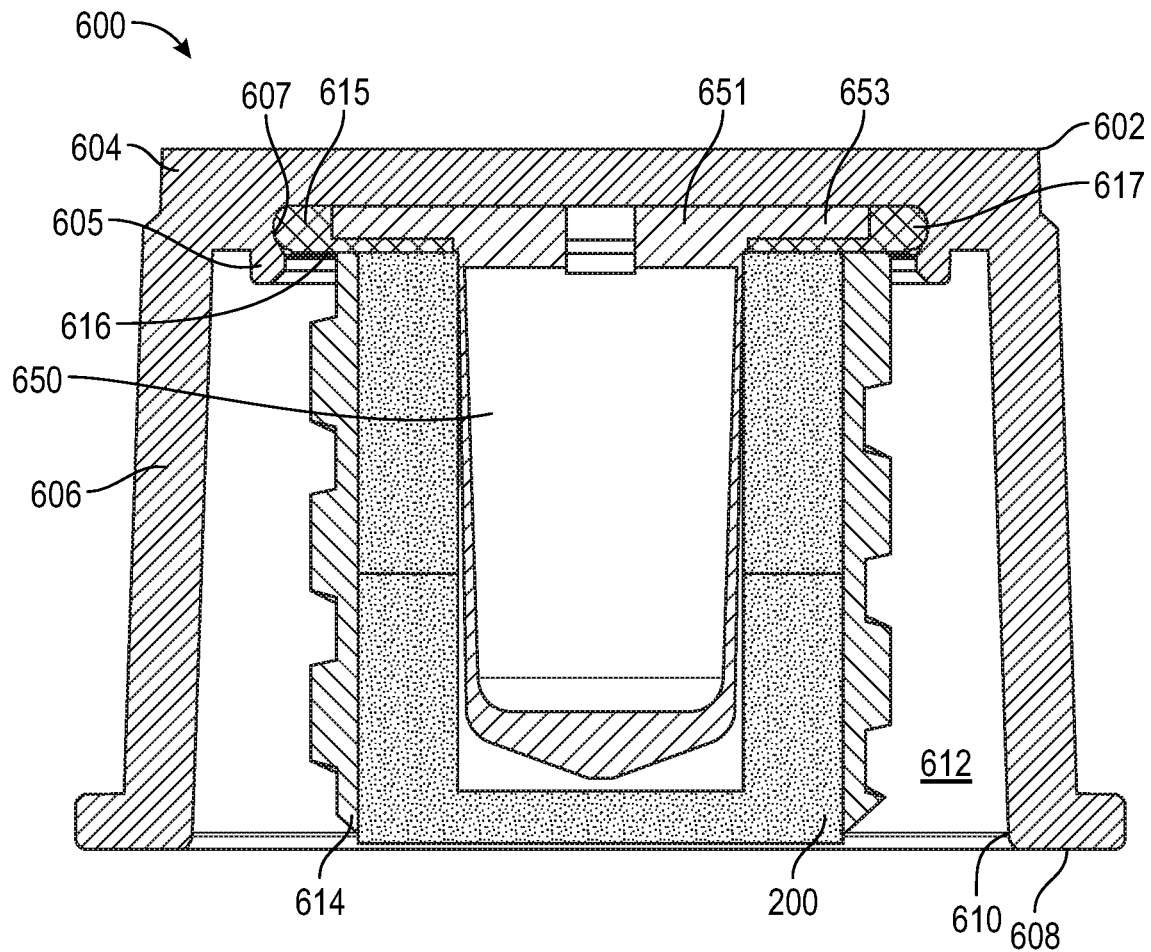

FIG. 23 diagrammatically illustrates a cap 600 in a cross-section side view according to an embodiment. The cap 600 comprises a housing 602, a top wall 604, a substantially cylindrical sidewall 606, an open bottom 608 defining an opening 610, a protrusion 614, a flexible insert 650, and a disinfection sponge 200. The insert 650 resides in a hollow defined by the disinfection sponge 200, which in turn resides in the cavity defined by the inner surface of the protrusion 614. The sidewall 606 defines a cavity 612, which is available for receipt of a hub of a connector. The protrusion 614 is positioned within the first cavity 612 and can be essentially cylindrical and coaxial with the sidewall 606. The opening 610 is disposed at the open bottom 608 of the housing 602. An inner surface of the top wall 604 can form a top of cavity 612. In an embodiment, the protrusion 614 is integrally formed with the housing 602. In another embodiment, the protrusion 614 is attached to the top wall 604 of the housing 602 by, for example, a snap-fit attachment. In this embodiment, the top wall 604 comprises an elongate ring 605 having an interior surface 607. The flexible insert 650 comprises a top wall 651 with an extension 653. The protrusion 614 comprises an upper lip 615 that has a shoulder 616 and an edge 617. The upper lip 615 of the protrusion 614 fits into the elongate ring 605, where the edge 617 of the upper lip 615 engages with the interior surface 607 of the elongate ring 605. The extension 653 of the top wall 651 of the insert 650 resides in the shoulder 616 of the protrusion 614. In this embodiment, the protrusion 614 is formed separately from the housing 602 and is snap fit into the elongate ring 605.

In one or more embodiments, there are inner threads (not shown) on an inner surface of the protrusion 614 having a size and pitch to engage a threaded fitting of a female connector, such as for example, a female Luer connector. Such connectors are generally and commonly used as catheter and other fluid-tight protective connectors in medical applications. The inner threads are sufficient to interlock with a mating feature of the female needleless connector such as a threaded fitting with male threads. There are also outer threads 624 are sufficient to interlock with a mating feature of a male needleless connector such as a threaded fitting with female threads. In one or more embodiments, the protrusion 614 can include one or more cantilevered prongs separated by one or more respective gaps. In one or more embodiments, at least one of the prongs can be configured to bend to facilitate interference fit between the protrusion and the mating feature of a male needleless connector or female needleless connector. In one or more embodiments, protrusion 614 can extend essentially from an inner surface of the top wall 604 toward the open bottom 608 of the housing 602. In one or more embodiments, the protrusion 614 can extend essentially parallel to the sidewall 606 of the housing.

In an exemplary implementation, a peel seal can be provided to seal the opening 610 prior to use of cap 600, for example, by attachment to a surface of a rim of the open bottom 608 of housing 602. In one or more embodiments, the peelable seal comprises an aluminum or multi-layer polymer film peel back top. In a specific embodiment, the peelable seal is heat-sealed or induction sealed to the open end of the cap. In one or more embodiments, the peelable seal comprises a moisture barrier. According to exemplary embodiments of the disclosure, the cap 600 can receive a tip or hub of a needleless connector, for example after the peel seal sealing cavity is removed or when the peal sealing film is pierced, within the cavity 612 and secure, for example, threadedly, the tip of the needleless connector within the cavity 612.

Figure 24:
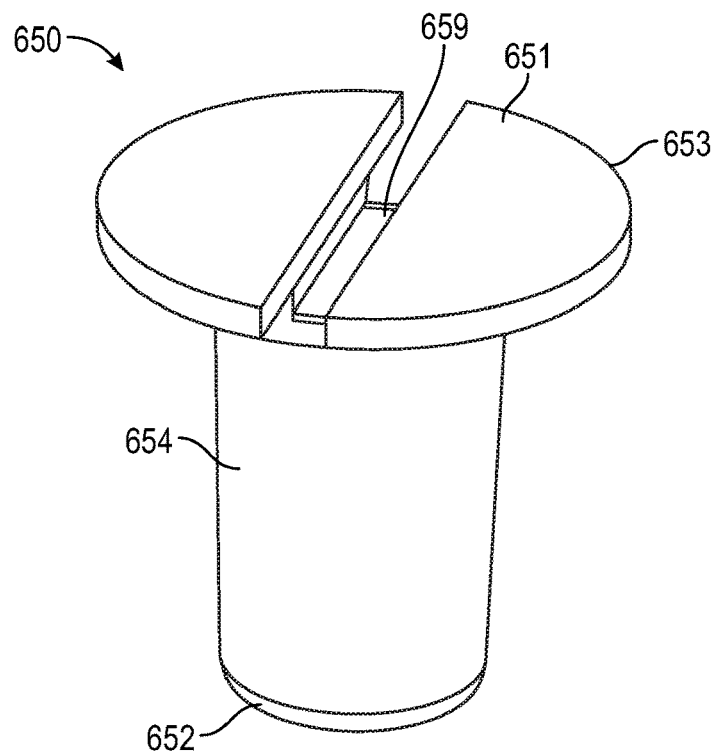
FIG. 24 illustrates a perspective top view of a flexible insert according to an embodiment.
Figure 25:
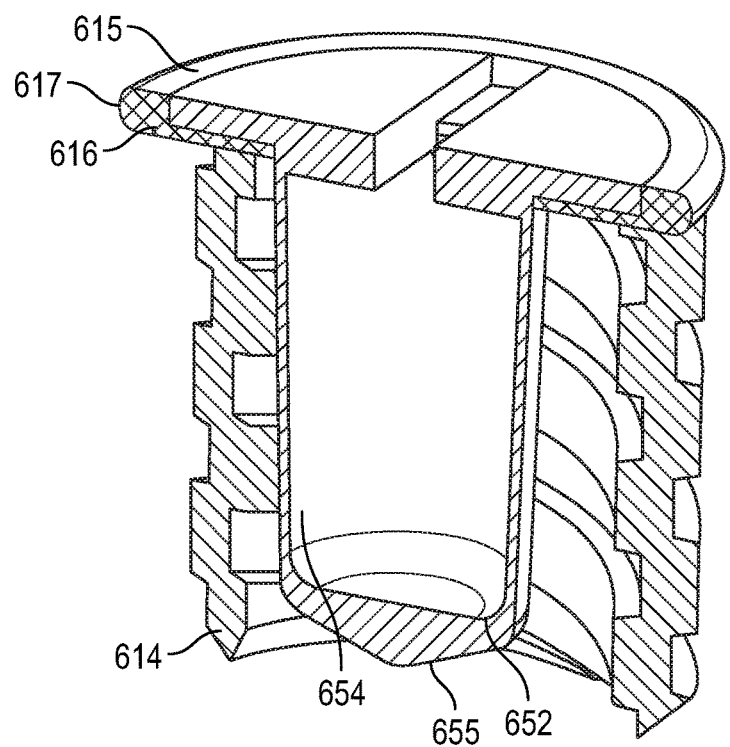
FIG. 25 illustrates a perspective cross-section view of the flexible insert according to FIG. 24 in combination with a protrusion according to an embodiment.

FIG. 24 illustrates a perspective top view of the flexible insert 650 and FIG. 25 illustrates a perspective cross-section view of the flexible insert 650 and the protrusion 614 of FIG. 23. The flexible insert 650 comprises a substantially cylindrical body having a bottom wall 652, which is closed and has the tapered surface 655, and the top edge 651 between which spans the sidewall 654. The top edge 651 may be configured to fit to cap designs as desired. In this embodiment, the flexible insert 650 comprises an attachment feature 659, which is a channel through a diameter of the top wall 651. The top wall 651 of the flexible insert 650 comprises an extension 653 that fits into the shoulder 616 of the protrusion 614. The edge 617 of the protrusion 614 engages with the elongate ring of the housing (item 605 of FIG. 23).

The external geometry of the flexible insert 650 is sufficiently complementary to open lumen Luer connectors for engaging. When the flexible insert 650 engages with an open lumen in Luer connectors such as a catheter or stopcock, the complementary inner Luer wall applies radial pressure on the insert to make an interference fit. The flexible insert 650 may define a cavity chamber inside the insert. Walls of the flexible insert 650 maybe breathable and/or porous, which may provide a channel, orifice or air path to connect the inside chamber to outside of the chamber of the insert to allow compression.

The flexible insert may be a solid material that is soft to compress longitudinally so when the cap is attached to male and closed female Luers such as needleless connectors and IV tubing end, it may retract toward a top wall at a closed end of cap housing, but rigid enough radially so it can form enough interference with open Luer such as catheters or stopcocks. This flexible insert is suitable for unisex disinfecting caps for use with various medical connectors as known by those skilled in the art, including those disclosed herein.

Analogously to the embodiments of FIGS. 20-22, upon assembly of the cap of FIG. 23 with a medical connector, male or female, a lumen edge pushes the sponge 200 toward the top wall 604 at a closed end of the housing 602, allowing disinfectant to be dispensed onto the lumen edge. When the insert 650 engages with the open lumen, a complementary inner wall, e.g. Luer wall, applies radial pressure on the insert 650 to make an interference fit with the inner wall, which mitigates and/or prevents disinfectant ingress into the lumen.

The caps herein (e.g., 100, 300, 600) can be made from any of a number of types of plastic materials such as polycarbonate, polypropylene, polyethylene, polyethylene terephthalate, polylactide, acrylonitrile butadiene styrene or any other moldable plastic material used in medical devices. In one or more embodiments, the caps comprise a polypropylene or polyethylene material.

According to exemplary implementations of the embodiments of the disclosure, caps herein can further comprise an outer housing implementing the safety features and designs described in U.S. patent applications No. 62/488,266 filed Apr. 21, 2017 and No. 62/523,506, filed Jun. 22, 2017, for example by modifying top walls, sidewalls, and/or housing.

According to yet further exemplary implementations of the embodiments of the disclosure, the caps herein (e.g., 100, 300, 600) can be implemented with various venting features and designs described in U.S. patent application Ser. Nos. 15/408,278 and 15/408,187, both filed on Jan. 17, 2017, for example by modifying shape and/or size of protrusion, and/or configuration (such as pitch, spacing, thickness, and/or other structural features) of inner threads and/or outer threads, and/or configuration of inner surface and/or outer surface.

In some embodiments, the medical connector comprises a needleless injection site, which may sometimes be referred to as a needleless injection port, hub, valve, or device, or as a needleless access site, port, hub, valve, or device, and which can include such brands as, for example, Clave® (available from ICU Medical, Inc.), SmartSite® (available from Cardinal Health, Inc.), and Q-Syte™ (available from Becton, Dickinson and Company). In some embodiments, the caps herein (e.g., 100, 300, 600) can be connected with any of a variety of different needleless injection sites, such as those previously listed. In one or more embodiments, after the cap has been coupled with connector, it is unnecessary to disinfect (e.g. treat with an alcohol swab) the connector prior to each reconnection of the connector with another connector, as the connector will be kept in an uncontaminated state while coupled with the cap. Use of the cap replaces the standard swabbing protocol for cleaning connectors.

A further aspect of the present disclosure pertains to a method of disinfecting a medical connector. The method comprises connecting the cap of one or more embodiments to a medical connector, wherein connecting includes engaging the threads of the medical connector onto the threads on the inner or outer surface of the second cavity of the cap upon insertion of the medical connector into the cap such that the medical connector contacts the absorbent material and the disinfectant or antimicrobial agent.

The exemplary caps of the present disclosure are capable of continuous disinfection of a connector and minimize ingress of microbial agents.

To avoid having to use different types of disinfecting caps to clean different types of connectors, exemplary caps (100, 300, 600) engage with male Luer connectors and also with female Luer connectors thereby allowing the user to clean different types of connectors with a single device. Upon mounting exemplary caps (100, 300, 600) onto female Luer connectors, the female Luer connectors is inserted into the second cavity and screwed onto the inner threads of the exemplary caps. Upon mounting the cap onto a male Luer connector, the male Luer connector is inserted into the second cavity and screwed onto the outer threads of the exemplary caps (100, 300, 600). The disinfectant of the disinfectant sponge contacts the female Luer connector after insertion of the female Luer connector into the second cavity of the exemplary caps (100, 300, 600). The disinfectant of the disinfectant sponge contacts the male Luer connector, the female Luer connector, and the hemodialysis connector after insertion of the connector into the second cavity of the exemplary caps (100, 300, 600).

Hence, the devices disclosed herein can be mounted onto both male and female Luer connectors, thus fulfilling a current need in the art.

A further aspect of the present disclosure pertains to an assembly. The assembly comprises the cap of one or more embodiments connected to a medical connector. In one or more embodiments, the medical connector is selected from a male Luer connector, a female Luer connector, and needleless connector.

EMBODIMENTS

Various numbered embodiments are listed below. It will be understood that the embodiments listed below may be combined with all aspects and other embodiments in accordance with the scope of the invention.

1. A cap comprising: a housing comprising: a top wall; an essentially cylindrical sidewall forming a first cavity; and an open bottom formed by the cylindrical sidewall with an opening to the first cavity within the housing for receiving a hub of a medical connector; and a protrusion extending from the housing and positioned within the first cavity, the protrusion having an inner surface and an outer surface, the inner surface of the protrusion defining a second cavity, an inner thread on the inner surface of the protrusion, the inner thread being sufficient to interlock with a threaded fitting of a female medical connector, and an outer thread on the outer surface of the protrusion, the outer thread being sufficient to interlock with a threaded fitting of a male medical connector; a disinfection sponge configured within the second cavity; and a pressure seal attached to the housing and disposed adjacent to a surface of the disinfection sponge.

2. The cap of embodiment 1, wherein upon engagement of the cap with the medical connector, the disinfection sponge contacts a lumen edge of the medical connector and the pressure seal blocks a lumen of the medical connector thereby inhibiting disinfectant ingress into the lumen.

3. The cap of embodiment 2, wherein when the lumen of the medical connector is open to the cap, the pressure seal enters the lumen to inhibit disinfectant ingress into the lumen.

4. The cap of embodiment 2, wherein when the medical connector comprises a septum in the lumen, the pressure seal is positioned to avoid creating a fluid path through the septum.

5. The cap of embodiment 1, wherein the disinfection sponge comprises a slotted end; an essentially cylindrical sponge sidewall defining a hollow and an open end; and a sponge end wall.

6. The cap of embodiment 5, wherein the slotted end of the disinfection sponge comprises a slot that extends into opposing portions of the sponge sidewall.

7. The cap of embodiment 6, wherein the slot extends along opposing portions of the sponge sidewall to the open end.

8. The cap of embodiment 5, wherein the pressure seal is disposed in the hollow of the disinfection sponge.

9. The cap of embodiment 8, wherein in an uncompressed state, the pressure seal is disposed entirely in the hollow.

10. The cap of embodiment 5, wherein the sponge end wall is in direct contact with an interior surface of the top wall.

11. The cap of embodiment 1, wherein the pressure seal comprises an elongate member and an insert, wherein: the elongate member extends from an interior surface of the top wall of the housing; and the insert comprises: a bottom wall, and an essentially cylindrical insert sidewall, the insert sidewall forming a chamber and a top edge of the insert sidewall defining an aperture; the insert slidably engaging with the elongate member.

12. The cap of embodiment 11, wherein an inside surface of the top edge slidably engages with the elongate member.

13. The cap of embodiment 11, wherein the elongate member comprises a shoulder section, a slanted section, and one or more sliding sections.

14. The cap of embodiment 11, wherein the insert comprises a plurality of prongs defined by portions of the insert sidewall and the top edge separated by slits.

15. The cap of embodiment 14, wherein faces of the prongs slidably engage with the elongate member.

16. The cap of embodiment 11, wherein an outside geometry of the insert sidewall comprises a tapered surface effective to complement an inner surface of a lumen of the medical connector.

17. The cap of embodiment 11, wherein the insert comprises a polymeric material selected from the group consisting of polyethylene, polypropylene, thermoplastic elastomer (TPE), or combinations thereof.

18. The cap of embodiment 1, wherein the pressure seal comprises a flexible insert attached to an interior surface of the top wall of the housing.

19. The cap of embodiment 18, wherein the flexible insert comprises an elastomeric polymeric material.

20. The cap of embodiment 18, wherein the flexible insert comprises a top wall, a bottom wall, and an essentially cylindrical and porous insert sidewall extending between the top wall and the bottom wall.

21. The cap of the preceding embodiment, wherein the top wall of the flexible insert further comprises an extension that engages with an upper lip the protrusion.

22. The cap of one of embodiments 18 to 21, wherein the flexible insert is breathable.

23. A cap comprising: a housing comprising: a top wall; an essentially cylindrical sidewall forming a first cavity; and an open bottom formed by the cylindrical sidewall with an opening to the first cavity within the housing for receiving a hub of a medical connector; and a protrusion extending from the housing and positioned within the first cavity, the protrusion having an inner surface and an outer surface, the inner surface of the protrusion defining a second cavity, an inner thread on the inner surface of the protrusion, the inner thread being sufficient to interlock with a mating feature of the medical connector comprising a female medical connector, and an outer thread on the outer surface of the protrusion, the outer thread being sufficient to interlock with a mating feature of the medical connector comprising a male medical connector; a disinfection sponge configured within the second cavity, the disinfection sponge comprising a slotted end; an essentially cylindrical sponge sidewall defining a hollow and an open end; and a sponge end wall; and a pressure seal disposed in the hollow of the disinfection sponge, the pressure seal comprising: an elongate member extending from an interior surface of the top wall of the housing; and an insert comprising a bottom wall, and an essentially cylindrical insert sidewall, the insert sidewall forming a chamber and a top edge of the insert sidewall defining an aperture; the insert slidably engaging with the elongate member; wherein upon engagement of the cap with the medical connector, the disinfection sponge contacts a lumen edge of the medical connector and the insert of the pressure seal blocks a lumen of the medical connector thereby inhibiting disinfectant ingress into the lumen.

24. The cap of embodiment 23, wherein an inside surface of the top edge slidably engages with the elongate member.

25. The cap of embodiment 23, wherein the elongate member comprises a shoulder section, a slanted section, and one or more sliding sections.

26. The cap of embodiment 23, wherein the insert sidewall comprises a plurality of prongs defined by portions of the insert sidewall and the top edge separated by slits.

27. The cap of embodiment 26, wherein faces of the prongs slidably engage with the elongate member.

28. The cap of embodiment 23, wherein an outside geometry of the insert sidewall comprises a tapered surface effective to compliment an inner surface of a lumen of the medical connector.

29. The cap of embodiment 23, wherein the insert comprises a polymeric material selected from the group consisting of polyethylene, polypropylene, thermoplastic elastomer (TPE), or combinations thereof.

30. A cap comprising: a housing comprising: a top wall; an essentially cylindrical sidewall forming a first cavity; and an open bottom formed by the cylindrical sidewall with an opening to the first cavity within the housing for receiving a hub of a medical connector; and a protrusion extending from the housing and positioned within the first cavity, the protrusion having an inner surface and an outer surface, the inner surface of the protrusion defining a second cavity, an inner thread on the inner surface of the protrusion, the inner thread being sufficient to interlock with a mating feature of the medical connector comprising a female medical connector, and an outer thread on the outer surface of the protrusion, the outer thread being sufficient to interlock with a mating feature of the medical connector comprising a male medical connector; a disinfection sponge configured within the second cavity, the disinfection sponge comprising a slotted end; an essentially cylindrical sponge sidewall defining a hollow and an open end; and a sponge end wall; and a pressure seal disposed in the hollow of the disinfection sponge, the pressure seal comprising: a flexible insert attached to an interior surface of the top wall of the housing; wherein upon engagement of the cap with the medical connector, the disinfection sponge contacts a lumen edge of the medical connector and the pressure seal blocks a lumen of the medical connector thereby inhibiting disinfectant ingress into the lumen.

31. The cap of embodiment 30, wherein the flexible insert comprises an elastomeric polymeric material.

32. The cap of embodiment 30, wherein the flexible insert comprises a top wall, a bottom wall, and an essentially cylindrical and porous insert sidewall extending between the top wall and the bottom wall.

33. The cap of the preceding embodiment, wherein the top wall of the flexible insert further comprises an extension that engages with an upper lip the protrusion.

34. The cap of one of embodiments 30 to 33, wherein the flexible insert is breathable.

35. The cap of any preceding embodiment, wherein the medical connector is selected from a male Luer connector, a female Luer connector, and a needleless connector.

36. The cap of any preceding embodiment, wherein the disinfection sponge comprises a disinfectant, an antimicrobial agent, or combinations thereof.

37. The cap of embodiment 36, wherein the disinfectant or the antimicrobial agent is selected from the group consisting essentially of: isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

38. The cap of embodiment 37, wherein the disinfectant or antimicrobial agent comprises at least one of chlorhexidine gluconate and chlorhexidine diacetate.

39. The cap of any of embodiments 1 to 38, wherein the protrusion is integrally-formed with the housing.

40. The cap of any of embodiments 1 to 38, wherein the protrusion is attached to an interior surface of the top wall of the housing.

41. The cap of the preceding embodiment, wherein the protrusion is snap-fix or adhered to the interior surface of the top wall of the housing.

42. The cap of the preceding embodiment, wherein the protrusion comprises an upper lip that engages with an elongate ring extending from an inner surface of the top wall of the housing.

43. A method of disinfecting a medical connector comprising: connecting the cap of any preceding embodiment to a medical connector by engaging threads of the medical connector onto the inner thread or the outer thread of the protrusion such that an edge of the medical connector contacts the disinfection sponge and the pressure seal inhibits disinfectant ingress into a lumen of the medical connector.

44. A medical assembly comprising the cap of any of embodiments 1 to 42 connected to a medical connector.

45. The medical assembly of embodiment 44, wherein the medical connector is a female medical connector with a male threaded fitting selected from the group consisting of: a needleless connector, a stopcock, a female Luer connector, and a catheter connector.

46. The medical assembly of embodiment 44, wherein the medical connector is a male medical connector with a female threaded fitting selected from the group consisting of: an intravenous tubing end and a male Luer connector.

While the present disclosure has been shown and described with reference to certain exemplary embodiments thereof, it will be understood by those skilled in the art that various changes in form and details may be made therein without departing from the spirit and scope of the embodiments of the present disclosure. For example, a disinfection sponge can comprise any suitable disinfecting or other application-specific substance, and can be made of any suitable material. Also, the inner and/or the outer housing of the cap can be single shot molded, or made by other suitable process. Furthermore, any of the features or elements of any exemplary implementations of the embodiments of the present disclosure as described above and illustrated in the drawing figures can be implemented individually or in any combination(s) as would be readily appreciated by skilled artisans without departing from the spirit and scope of the embodiments of the present disclosure.

In addition, the included drawing figures further describe non-limiting examples of implementations of certain exemplary embodiments of the present disclosure and aid in the description of technology associated therewith. Any specific or relative dimensions or measurements provided in the drawings other as noted above are exemplary and not intended to limit the scope or content of the inventive design or methodology as understood by artisans skilled in the relevant field of invention.

Other objects, advantages and salient features of the disclosure will become apparent to those skilled in the art from the details provided, which, taken in conjunction with the annexed drawing figures, disclose exemplary embodiments of the disclosure.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has provided a description with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A cap comprising:
   a housing comprising:
      a top wall;
      an essentially cylindrical sidewall forming a first cavity; and
      an open bottom formed by the cylindrical sidewall with an opening to the first cavity within the housing for receiving a hub of a medical connector; and
   a protrusion extending from the housing and positioned within the first cavity, the protrusion having an inner surface and an outer surface, the inner surface of the protrusion defining a second cavity,
      an inner thread on the inner surface of the protrusion, the inner thread being sufficient to interlock with a threaded fitting of a female medical connector, and
      an outer thread on the outer surface of the protrusion, the outer thread being sufficient to interlock with a threaded fitting of a male medical connector;
   a disinfection sponge configured within the second cavity; and
   a pressure seal attached to the housing and disposed adjacent to a surface of the disinfection sponge.

2. The cap of claim 1, wherein upon engagement of the cap with the medical connector, the disinfection sponge contacts a lumen edge of the medical connector and the pressure seal blocks a lumen of the medical connector thereby inhibiting disinfectant ingress into the lumen.

3. The cap of claim 2, wherein when the lumen of the medical connector is open to the cap, the pressure seal enters the lumen to inhibit disinfectant ingress into the lumen.

4. The cap of claim 2, wherein when the medical connector comprises a septum in the lumen, the pressure seal is positioned to avoid creating a fluid path through the septum.

5. The cap of claim 1, wherein the disinfection sponge comprises a slotted end; an essentially cylindrical sponge sidewall defining a hollow and an open end; and a sponge end wall.

6. The cap of claim 5, wherein the slotted end of the disinfection sponge comprises a slot that extends into opposing portions of the sponge sidewall.

7. The cap of claim 6, wherein the slot extends along opposing portions of the sponge sidewall to the open end.

8. The cap of claim 5, wherein the pressure seal is disposed in the hollow of the disinfection sponge.

9. The cap of claim 8, wherein in an uncompressed state, the pressure seal is disposed entirely in the hollow.

10. The cap of claim 5, wherein the sponge end wall is in direct contact with an interior surface of the top wall.

11. The cap of claim 1, wherein the pressure seal comprises an elongate member and an insert, wherein:
    the elongate member extends from an interior surface of the top wall of the housing; and
    the insert comprises: a bottom wall, and an essentially cylindrical insert sidewall, the insert sidewall forming a chamber and a top edge of the insert sidewall defining an aperture;
    the insert slidably engaging with the elongate member.

12. The cap of claim 11, wherein an inside surface of the top edge slidably engages with the elongate member.

13. The cap of claim 11, wherein the elongate member comprises a shoulder section, a slanted section, and one or more sliding sections.

14. The cap of claim 11, wherein the insert comprises a plurality of prongs defined by portions of the insert sidewall and the top edge separated by slits.

15. The cap of claim 14, wherein faces of the prongs slidably engage with the elongate member.

16. The cap of claim 11, wherein an outside geometry of the insert sidewall comprises a tapered surface effective to complement an inner surface of a lumen of the medical connector.

17. The cap of claim 11, wherein the insert comprises a polymeric material selected from the group consisting of polyethylene, polypropylene, thermoplastic elastomer (TPE), or combinations thereof.

18. The cap of claim 1, wherein the pressure seal comprises a flexible insert attached to an interior surface of the top wall of the housing.

19. The cap of claim 18, wherein the flexible insert comprises an elastomeric polymeric material.

20. The cap of claim 18, wherein the flexible insert comprises a top wall, a bottom wall, and an essentially cylindrical and porous insert sidewall extending between the top wall and the bottom wall.

21. The cap of claim 18, wherein the top wall of the flexible insert further comprises an extension that engages with an upper lip of the protrusion.

22. The cap of claim 18, wherein the flexible insert is breathable.

23. A cap comprising:
   a housing comprising:
      a top wall;
      an essentially cylindrical sidewall forming a first cavity; and
      an open bottom formed by the cylindrical sidewall with an opening to the first cavity within the housing for receiving a hub of a medical connector; and
   a protrusion extending from the housing and positioned within the first cavity, the protrusion having an inner surface and an outer surface, the inner surface of the protrusion defining a second cavity,
      an inner thread on the inner surface of the protrusion, the inner thread being sufficient to interlock with a mating feature of the medical connector comprising a female medical connector, and
      an outer thread on the outer surface of the protrusion, the outer thread being sufficient to interlock with a mating feature of the medical connector comprising a male medical connector;
   a disinfection sponge configured within the second cavity, the disinfection sponge comprising a slotted end; an essentially cylindrical sponge sidewall defining a hollow and an open end; and a sponge end wall; and
   a pressure seal disposed in the hollow of the disinfection sponge, the pressure seal comprising:
      an elongate member extending from an interior surface of the top wall of the housing; and
      an insert comprising a bottom wall, and an essentially cylindrical insert sidewall, the insert sidewall forming a chamber and a top edge of the insert sidewall defining an aperture; the insert slidably engaging with the elongate member;
   wherein upon engagement of the cap with the medical connector, the disinfection sponge contacts a lumen edge of the medical connector and the insert of the pressure seal blocks a lumen of the medical connector thereby inhibiting disinfectant ingress into the lumen.

24. The cap of claim 23, wherein an inside surface of the top edge slidably engages with the elongate member.

25. The cap of claim 23, wherein the elongate member comprises a shoulder section, a slanted section, and one or more sliding sections.

26. The cap of claim 23, wherein the insert sidewall comprises a plurality of prongs defined by portions of the insert sidewall and the top edge separated by slits.

27. The cap of claim 26, wherein faces of the prongs slidably engage with the elongate member.

28. The cap of claim 23, wherein an outside geometry of the insert sidewall comprises a tapered surface effective to compliment an inner surface of a lumen of the medical connector.

29. The cap of claim 23, wherein the insert comprises a polymeric material selected from the group consisting of polyethylene, polypropylene, thermoplastic elastomer (TPE), or combinations thereof.

* * * * *